United States Patent
Lee et al.

(10) Patent No.: US 6,704,439 B1
(45) Date of Patent: Mar. 9, 2004

(54) METHOD FOR IDENTIFICATION OF ALVEOLAR NERVE REGION IN MANDIBLE IMAGE

(75) Inventors: Heu-yeon Lee, Seoul (KR); Chan-kyung Lee, Seoul (KR); Chang-hwan Kong, Seoul (KR)

(73) Assignee: 10DR Co. Ltd., Seoul (KR)

( * ) Notice: Subject to any disclaimer, the term of this patent is extended or adjusted under 35 U.S.C. 154(b) by 518 days.

(21) Appl. No.: 09/661,216

(22) Filed: Sep. 14, 2000

(30) Foreign Application Priority Data

Sep. 14, 1999 (KR) ......................... 1999-39328

(51) Int. Cl.[7] .................................................. G06K 9/00
(52) U.S. Cl. ...................... 382/131; 382/180; 382/194; 382/224
(58) Field of Search .................. 382/128, 131, 382/132, 168, 169, 171, 172, 180, 194, 224, 225, 237

(56) References Cited

U.S. PATENT DOCUMENTS

| 4,920,573 | A | * | 4/1990 | Rhodes et al. | 382/131 |
| 5,725,376 | A | * | 3/1998 | Poirier | 433/172 |
| 5,848,177 | A | * | 12/1998 | Bauer et al. | 382/128 |
| 6,466,687 | B1 | * | 10/2002 | Uppaluri et al. | 382/128 |

OTHER PUBLICATIONS

"Unsupervised Segmentation Based on Robust Estimation and Coocurrence Data" by Martinez–Perez et al. IEEE Image Processing, 1996. Proceedings., International Conference on, vol.: 3, Sep. 16–19, 1996 page(s): 943–945 vol. 3.*

* cited by examiner

Primary Examiner—Jon Chang
Assistant Examiner—Charles Kim
(74) Attorney, Agent, or Firm—Knobbe, Martens, Olson & Bear, LLP

(57) ABSTRACT

A method of identifying an alveolar nerve region in a mandible image for dental implantation. The method includes: (a) slicing the 3-dimensional mandible image into a number of 2-dimensional slice images; (b) detecting a binary image object corresponding to a mandible region from one of the slice images; (c) grouping pixels of the binary image object of the mandible region into clusters each containing pixels having a similar intensity; (d) determining clusters that have pixels more than a predetermined minimum number of pixels, and determining the minimum labeled cluster having the lowest pixel intensity distribution among the clusters; (e) composing a new binary image containing pixels which belong to both the mandible region and the clusters having intensity distribution lower than that of the minimum labeled cluster, to extract a candidate nerve object; and (f) determining whether the candidate nerve object corresponds to the real alveolar nerve region. Therefore, the method allows a dental surgeon to accurately detect the position of the alveolar nerve region during an implantation in an automated manner.

23 Claims, 21 Drawing Sheets

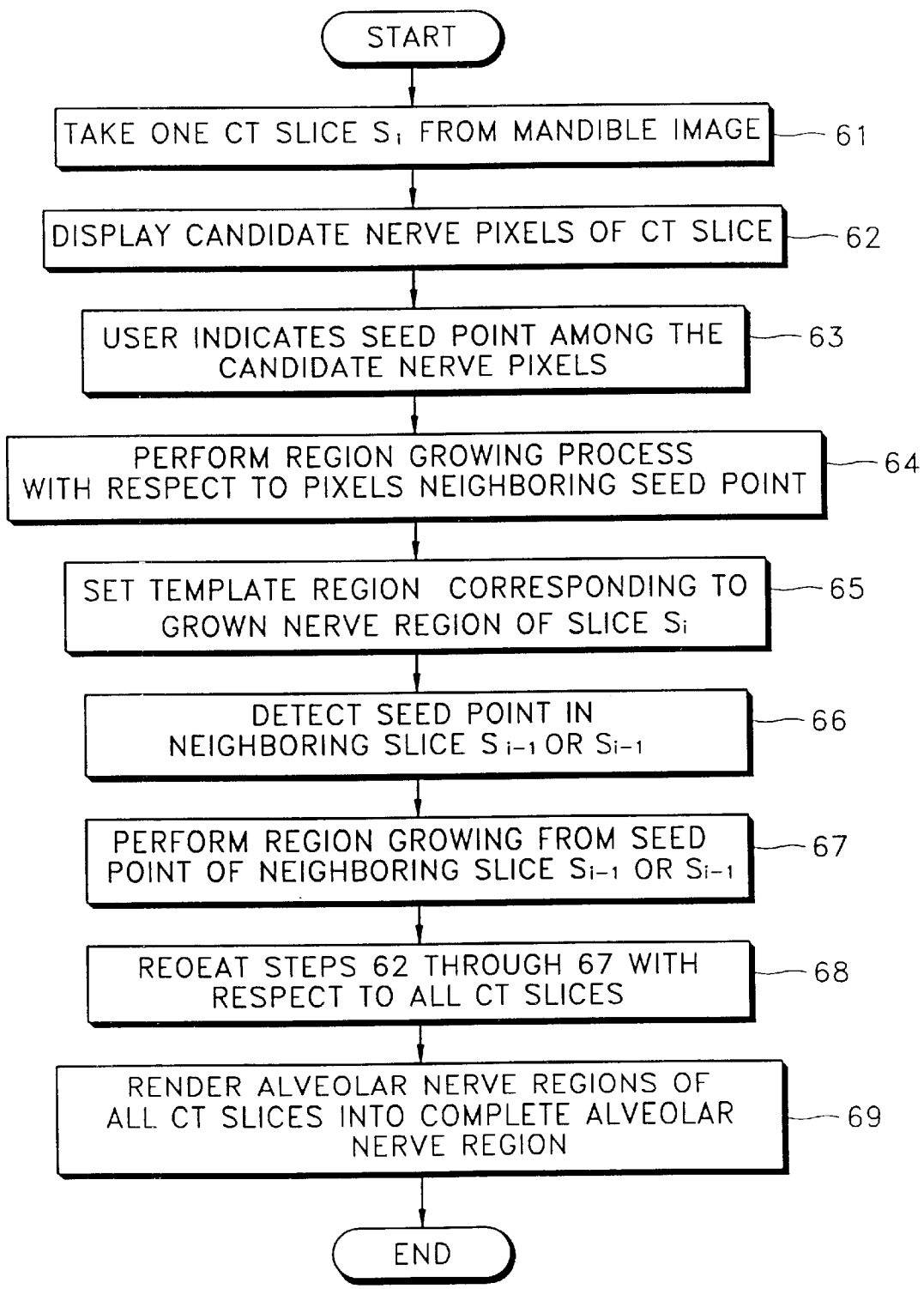

METHOD FOR IDENTIFICATION OF ALVEOLAR NERVE REGION IN MANDIBLE IMAGE

CROSS-REFERENCE TO RELATED APPLICATIONS

Applicants claim priority under 35 U.S.C. §119 from Korean Patent Application No. 1999-39328, filed Sep. 14, 1999, and entitled "Method for Identification of Alveolar Never Region in Mandible Region."

BACKGROUND OF THE INVENTION

1. Field of the Invention

The present invention relates to a method for identifying an alveolar nerve region in a mandible image during dental implantation, and more particularly, to an automated or semi-automated method for identifying an alveolar nerve region in a mandible image obtained through computed tomography (CT).

2. Description of the Related Art

For cases where damage to teeth is too serious to repair, surgery for substituting artificial teeth for damaged teeth has become common. For such surgery, an implant screw for supporting the artificial teeth must be inserted into the jawbone.

FIGS. 1A through 1G illustrate each step of implantation. In detail, in the case where a tooth is extracted due to damage as shown in FIG. 1A, an artificial tooth is implanted into the damaged region as follows. The gum in the damaged region is cut as shown in FIG. 1B, a region into which an implant screw is to be inserted is drilled to form a hole as shown in FIG. 1C, and the implant screw is inserted into the hole as shown in FIG. 1D. Then, the implanted region is left to allow the implant screw to firmly bind with the jawbone and new tissue to cover the implant screw, as shown in FIG. 1E. When the implant screw has firmly bound to the jawbone, the gum on the top of the implanted region is removed as shown in FIG. 1F and then an artificial tooth is mounted on the implant screw.

However, if a dentist fails to insert the implant screw into an appropriate region in an accurate direction during the above surgery, the implant screw cannot satisfactorily support the artificial tooth or the inappropriately inserted implant screw may encroach on alveolar nerves, causing facial paralysis. Thus, the most important step in implantation is to accurately assess the density of the jawbone in the vicinity of a desired implantation site. In particular, contact between the implant screw and a low-density area and encroachment on the nerves in the jawbone must be avoided. Thus, it is important for a dental surgeon to inspect accurately the location of the nerves near a desired implant site.

Success in implantation depends on how accurately a dental surgeon knows the jawbone density of a patient. The current leading method in accurately ascertaining the jawbone density is computed tomography (CT). CT refers to when an object is scanned in many directions to acquire a 3-dimensional image of the object. At a dental surgery, during CT scanning, either the maxilla or the mandible is typically scanned in 1.0-mm increments, resulting in about 45 image slices.

FIG. 2 shows an image of a mandible obtained by CT. As shown in FIG. 2, the CT scanning and computer simulation technique provide a large amount of information on the mandible to a dental surgeon. However, it is not easy for the dental surgeon to directly and accurately identify the location of the nerves from the CT images.

SUMMARY OF THE INVENTION

To solve the above problems, it is an objective of the present invention to provide an automated method for identifying an alveolar nerve region in a mandible image obtained by computed tomography (CT).

It is another objective of the present invention to provide a method for identifying an alveolar nerve region from a mandible image obtained by CT, using a seed point present in a CT slice.

It is another objective of the present invention to provide computer readable media for the alveolar nerve identification methods.

According to an aspect of the present invention, there is provided a method of identifying an alveolar nerve region in a mandible image, comprising the steps of: (a) slicing the 3-dimensional mandible image into a number of 2-dimensional slice images; (b) detecting a binary image object corresponding to a mandible region from one of the slice images; (c) grouping pixels of the binary image object of the mandible region into clusters each containing pixels having a similar intensity; (d) determining clusters that have pixels more than a predetermined minimum number of pixels, and determining the minimum labeled cluster having the lowest pixel intensity distribution among the clusters; (e) composing a new binary image containing pixels which belong to both the mandible region and the clusters having intensity distribution lower than that of the minimum labeled cluster, to extract a candidate nerve object; and (f) determining whether the candidate nerve object corresponds to the real alveolar nerve region.

The alveolar nerve region identification method may further comprise determining candidate nerve objects for the real alveolar nerve region with respect to all of the slice image, and assembling all of the slice images into a mandible image to produce a complete alveolar nerve region in the mandible image using the candidate nerve objects. Also, the method may further comprise identifying an alveolar nerve region for a neighboring slice image $S_{i-1}$ or $S_{i+1}$, which is located before or after the slice image $S_i$ by growing the alveolar nerve region determined from the slice $S_i$.

Preferably, step (f) comprises: (f1) performing a dilation operation on the candidate nerve object to extract the perimeter region thereof; (f2) comparing the intensity of the pixels belonging to the perimeter region with the intensity of the inner pixels surrounded by the perimeter region; and (f3) determining an object having a perimeter region whose pixel intensity is greater than that of the inner pixels, as a new candidate nerve object. Alternatively, step (f) may comprise: (f1) calculating the number $N_1$ of pixels belonging to the candidate nerve object; (f2) calculating the centroid point of the candidate nerve object; (f3) performing a region growing operation on the candidate nerve object, starting from the centroid point as a seed point to produce a grown nerve object; (f4) calculating the number $N_2$ of pixels of the grown nerve object; and (f5) comparing $N_1$ and $N_2$, and if $N_2$ is greater than $N_1$ by a predetermined number or more, removing the candidate nerve object. In another embodiment, step (f) may comprise: (f1) calculating a centroid point with respect to all of the pixels belonging to the mandible region of the slice image; (f2) determining the uppermost and lowermost pixels of the mandible region, and calculating a halfway point between the uppermost and lowermost pixels;

(f3) determining whether the centroid point is located near the halfway point; and (f4) if the centroid point is located near the halfway point, determining the candidate nerve object above the halfway point and nearest to the centroid point, or the candidate nerve object below and nearest to the centroid point, to be a real alveolar nerve region, and if the centroid point is not near the halfway point, determining the candidate nerve object nearest to the centroid point to be an alveolar nerve region.

According to another aspect of the present invention, there is provided a method of identifying an alveolar nerve region in a mandible image, comprising the steps: (a) slicing the 3-dimensional mandible image into a number of 2-dimensional slice images, and selecting one of the slice images; (b) displaying candidate nerve pixels of the selected slice image, one of the candidate nerve pixels being selected as a seed point to be used in identifying the alveolar nerve region of the slice image; (c) a user determining the seed point among the candidate nerve pixels; and (d) comparing the intensity of the seed point with the intensity of neighboring pixels, and performing a region growing process on the slice image based on whether a difference between the compared intensities is within a predetermined error range, to detect pixels corresponding to an alveolar nerve region of the slice image.

Preferably, the alveolar nerve identification method further comprises identifying an alveolar nerve region for a neighboring slice image $S_{i-1}$ or $S_{i+1}$, which is located before or after the slice image $S_i$, by growing the alveolar nerve region determined from the slice image $S_i$. Also, the method may comprise performing steps (a) through (d) with respect to each of the slice images to detect alveolar nerve regions, and assembling all of the slice images into a mandible image to produce a complete alveolar nerve region in the mandible image using the detected alveolar regions.

BRIEF DESCRIPTION OF THE DRAWINGS

The above objectives and advantages of the present invention will become more apparent by describing in detail preferred embodiments thereof with reference to the attached drawings in which:

FIG. 6 is a flowchart illustrating another embodiment of the method for identifying an alveolar nerve region in a CT image of a mandible according to the present invention;

DETAILED DESCRIPTION OF THE INVENTION

Figure 1A:
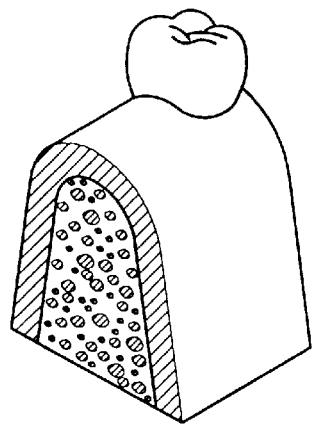
FIGS. 1A through 1G illustrate each step of dental implantation.
Figure 1B:
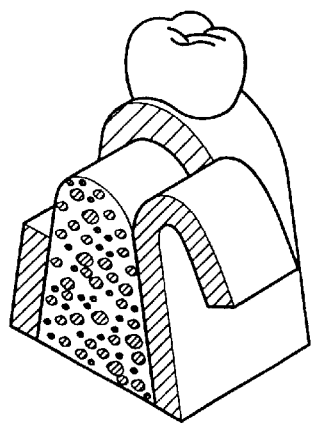
Figure 1C:
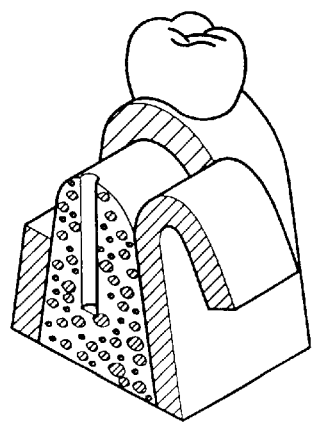
Figure 1D:
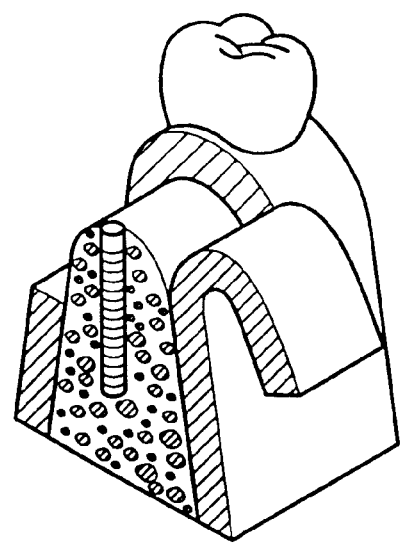
Figure 1E:
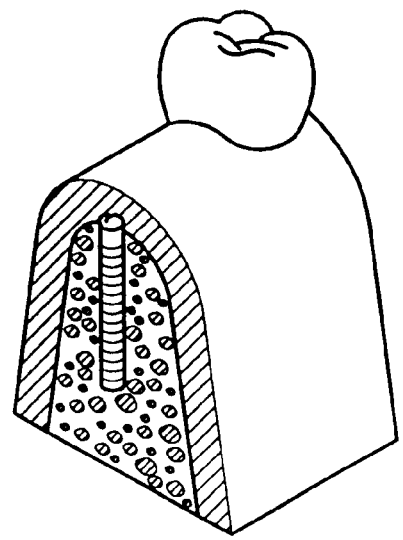
Figure 1F:
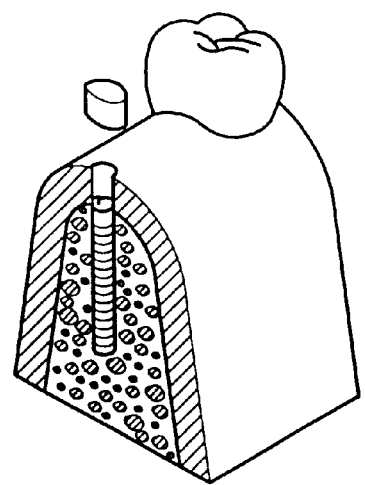
Figure 1G:
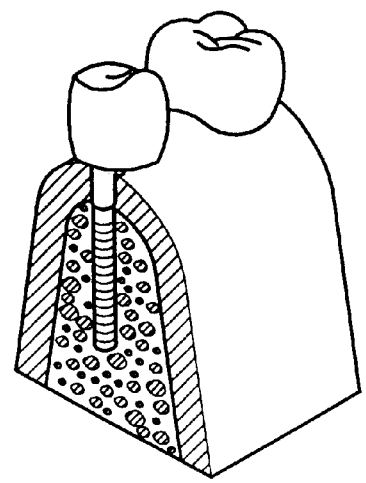
Figure 2:
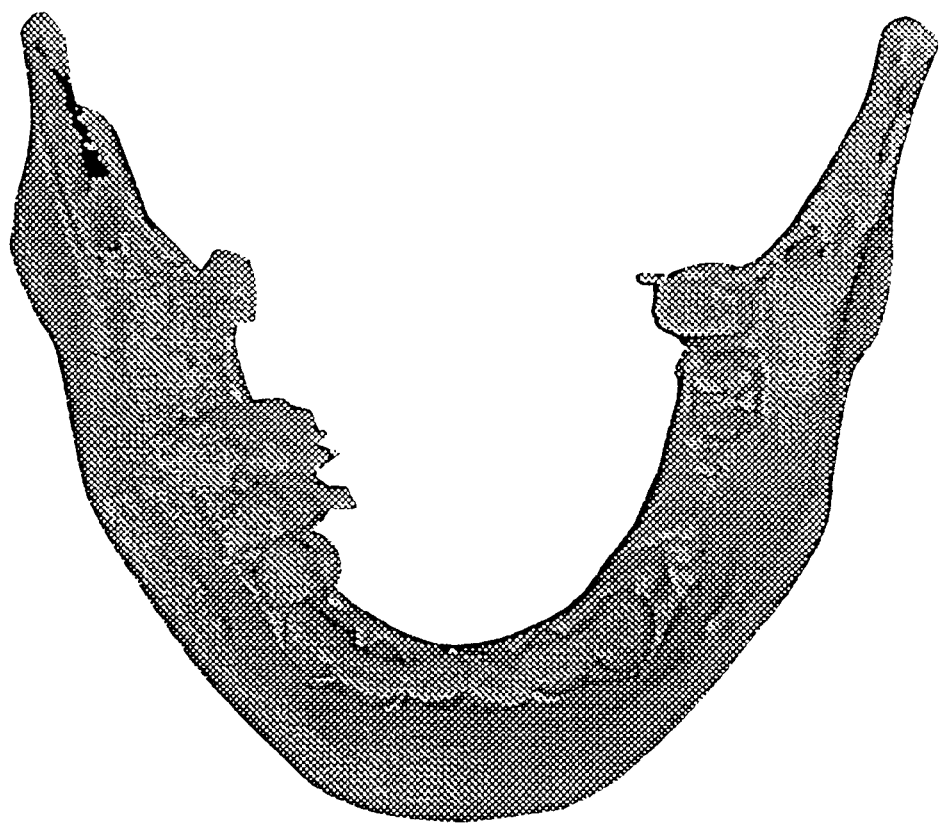
FIG. 2 shows a 3-dimensional image of a mandible obtained by computed tomography (CT)

In the present invention, a mandible region is distinguished in CT slices based on the intensity distribution of the region, and candidate nerve regions, which are considered to be real alveolar nerves in the mandible, are extracted from the mandible region. Then, the candidate nerve regions are subjected to a series of image processes to remove the candidate alveolar nerve regions which have low possibilities of being real alveolar nerves. The image processes used includes morphological operations, contrast enhancement, K-means clustering, and region growing image processing algorithms. The ultimate output image is expressed as a binary image, which illustrates the shape, size and location of the identified alveolar nerve region.

The terms to be used through the following embodiments are defined as follows. The term "object" refers to a group of binary pixels spatially adjacent or connected to each other. The term "perimeter" refers to a set of the outermost binary pixels of an object, the outermost binary pixels being connected to form a closed loop. The term "centroid point" refers to the mean position of all pixels constituting an object. The term "cluster" refers to a set of pixels having similar characteristics, for example, having a similar density.

Also, the image processing to be adopted in the following embodiments is briefly explained. First, "morphological operations" refer to a mathematical tool for processing and manipulating a set of objects, including dilation, erosion, closing and opening operations with respect to a binary image. The dilation operation expands the bright regions of the original image and contracts the dark regions thereof, so that the overall image appears brighter and larger. In contrast to the dialation operation, the erosion operation expands the dark regions of the original image and contracts the bright regions thereof, so that the overall image appears darker and smaller. The degree of expansion or contraction of the original image by the dilation or erosion operation varies according to the size and value of an operator referred to as a structure element. The opening and closing operations are performed in combination with the dilation and erosion operations. Here, the opening operation is for smoothing a region where the brightness sharply increases, whereas the closing operation is for smoothing a region where the brightness sharply drops.

Second, "contrast enhancement" refers to linearly scaling an image to place the intensity of the image between predetermined maximum and minimum values. Third, "K-means clustering" refers to assigning the pixels of an input image to a plurality of K groups (clusters) according to the similarity of intensity. In particular, a user defines K mean intensity values for K clusters and then each pixel of an image is assigned to the cluster having the mean intensity closest to the intensity of the pixel. After this clustering has taken place for all pixels, the mean intensity of the pixels which belong to each cluster are computed. Then, the results are defined as the new mean intensity for each cluster. Following this, the pixels of the image are reassigned to corresponding clusters based on the new mean intensities of the clusters. These processes are iterated until the mean intensity of each cluster shows the least change.

Fourth, "region growing" refers to determining a seed pixel for each cluster and grouping neighboring pixels having an intensity within a predetermined tolerance with respect to the seed pixel intensity, into the corresponding cluster. The mean intensity of the pixels contained in each cluster is computed again after a predetermined period of time, and each pixel of the image is reassigned to the corresponding cluster based on the new mean intensities.

Figure 3A:
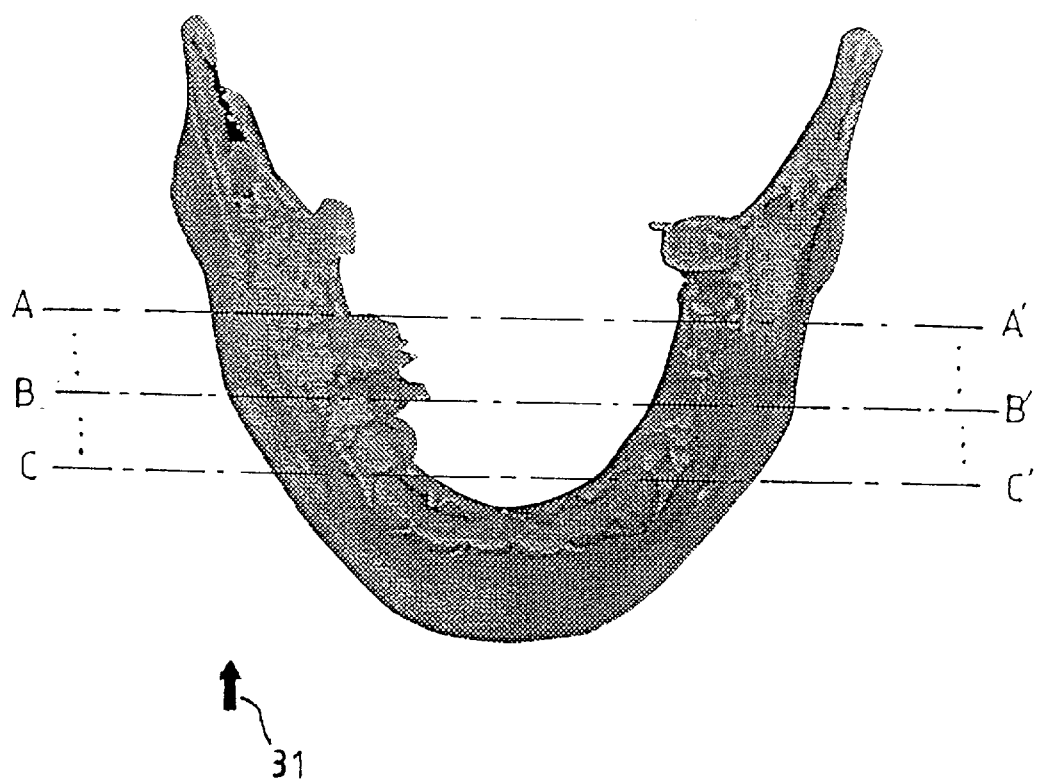
FIGS. 3A and 3B are diagrams illustrating a technique for obtaining slices from a 3-dimensional CT image of a mandible, which is applied to identify an alveolar nerve region in the CT image according to the present invention.
Figure 3B:
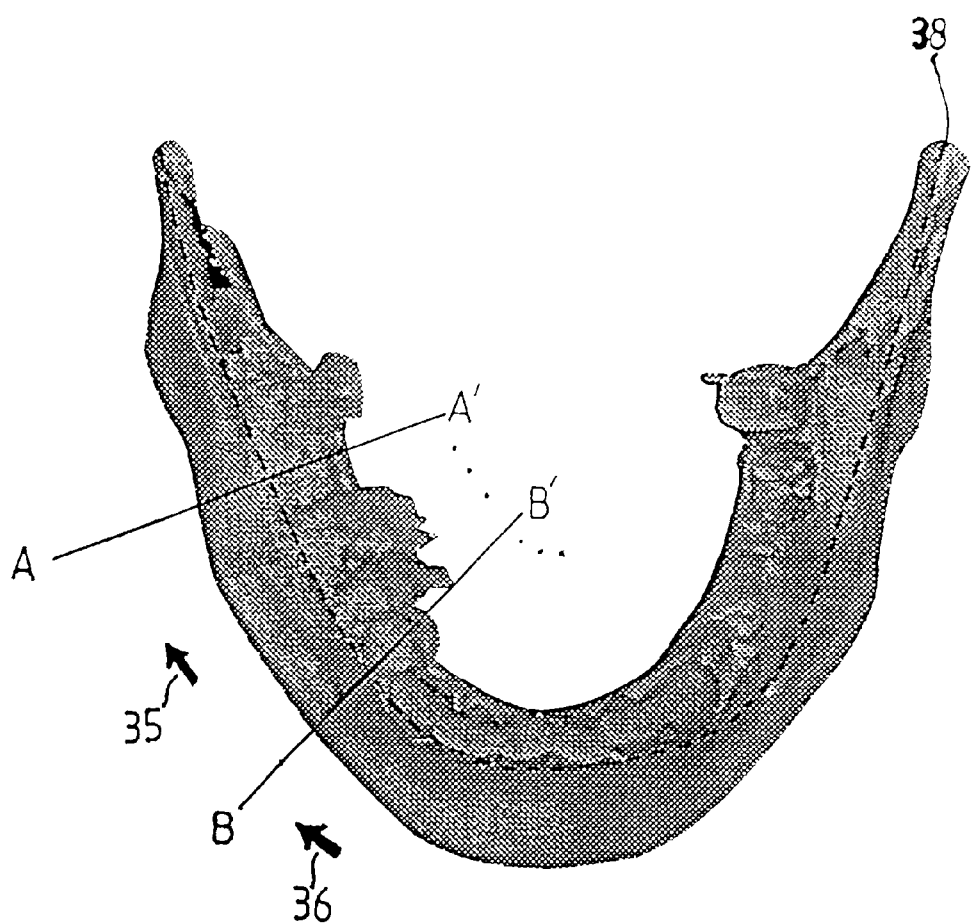

FIGS. 3A and 3B are diagrams illustrating a technique for obtaining slices from a 3-dimensional CT image of a mandible, which is applied to identify an alveolar nerve region in the CT image according to the present invention.

Figures 1, 4A:
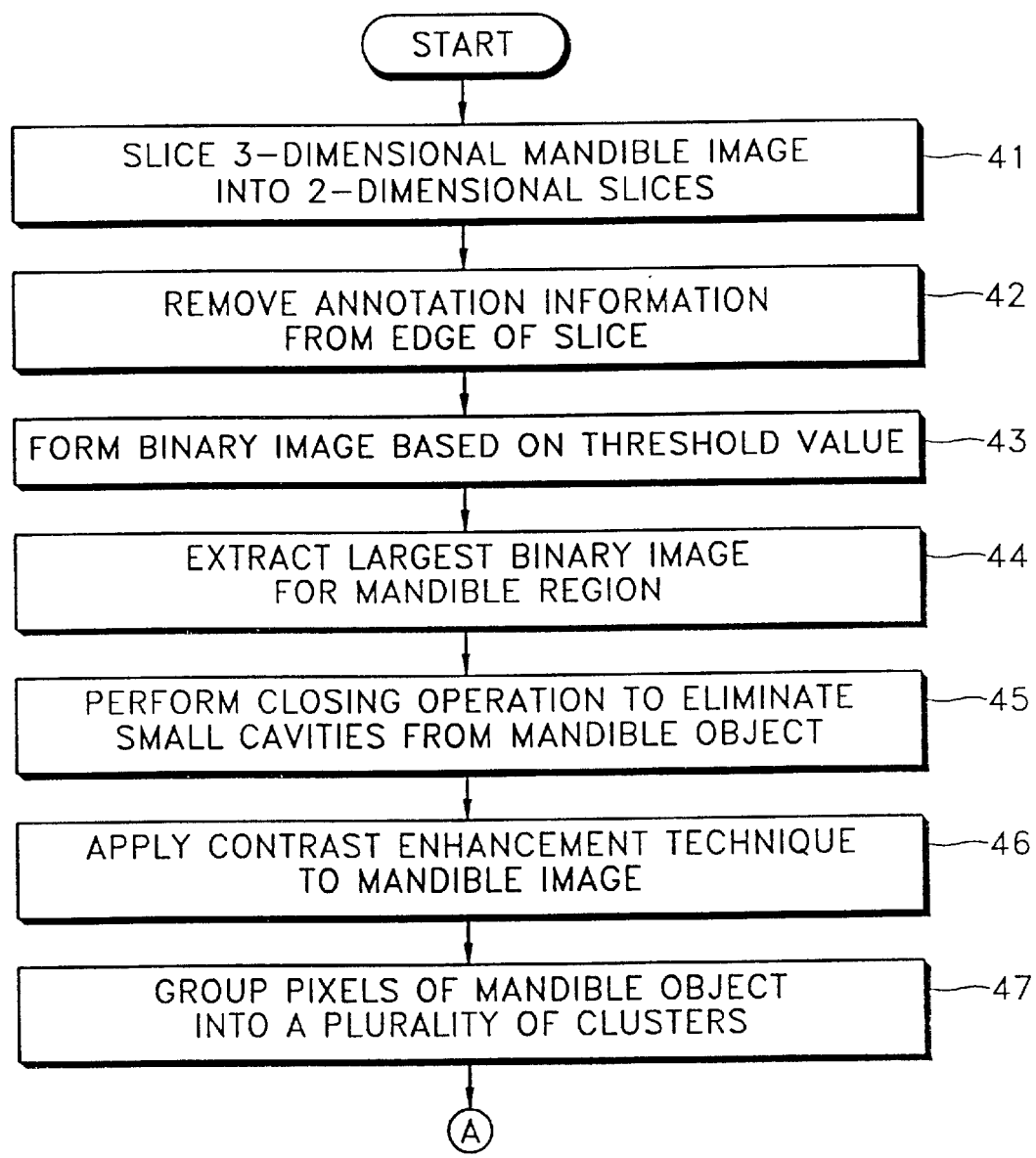
FIGS. 4A through 4D are flowcharts illustrating a method for identifying an alveolar nerve region in a CT slice image of a mandible according to a preferred embodiment of the present invention.
Figures 2, 4A:
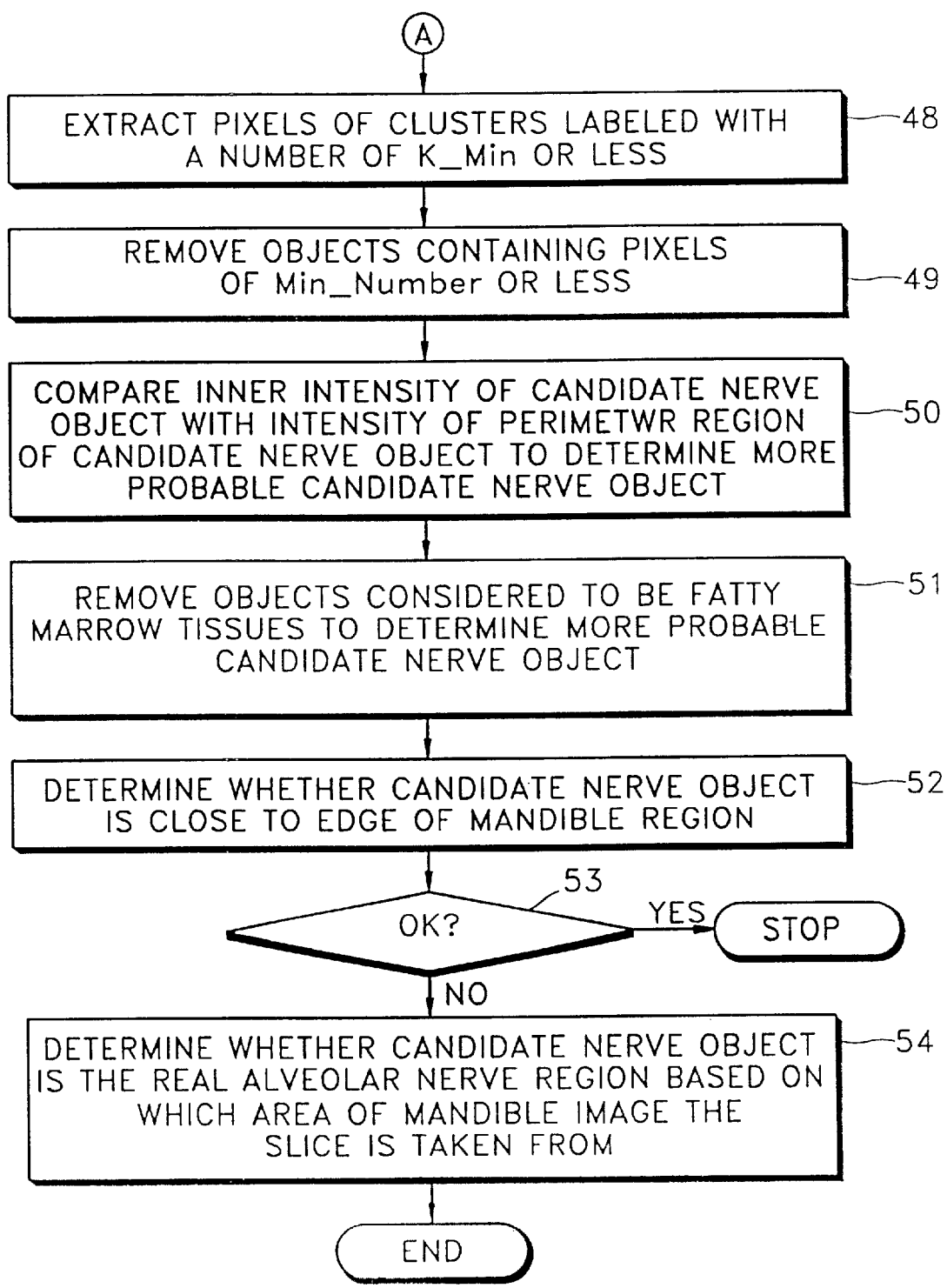
Figure 4B:
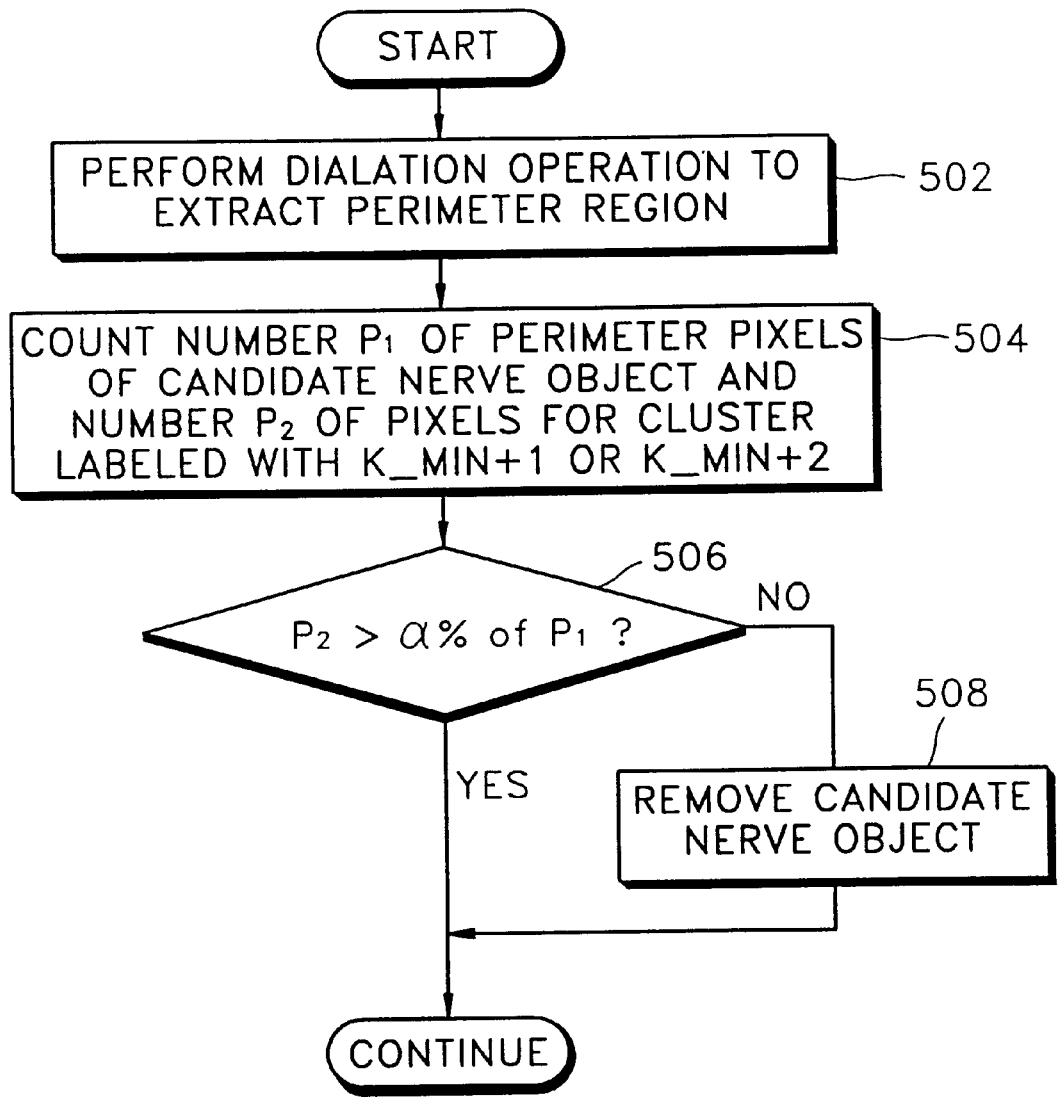
Figure 4C:
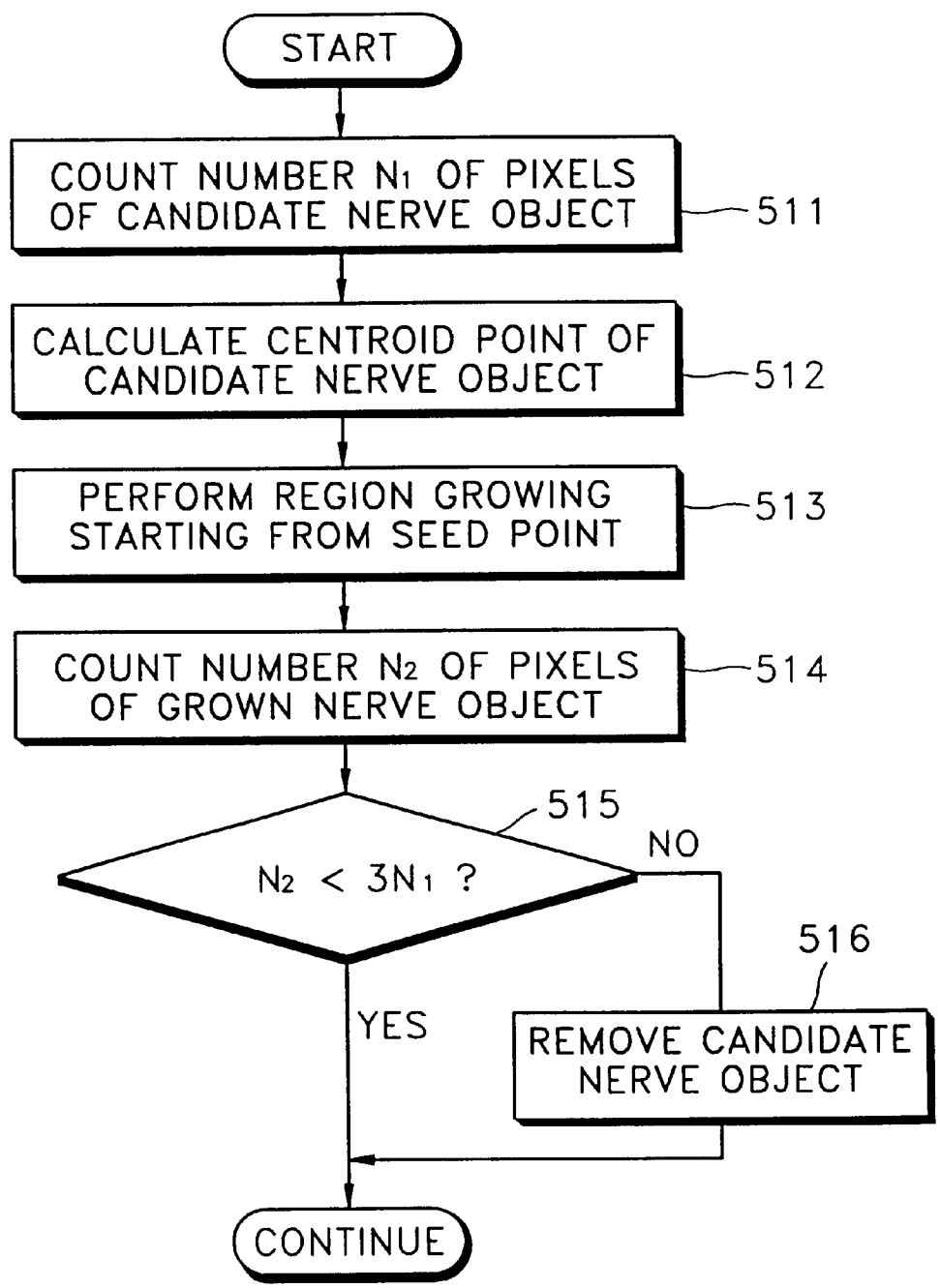
Figure 4D:
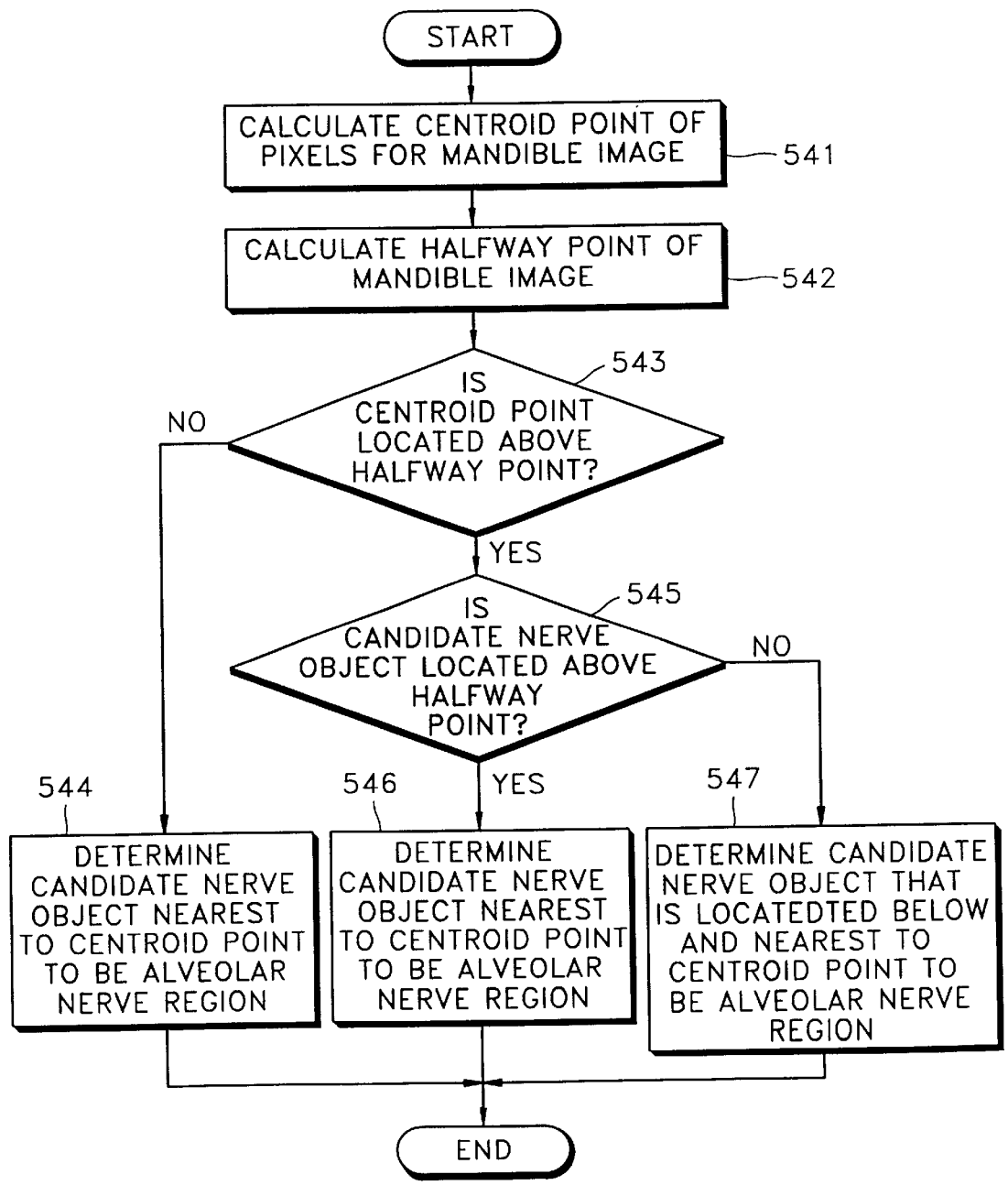
Figure 5A:
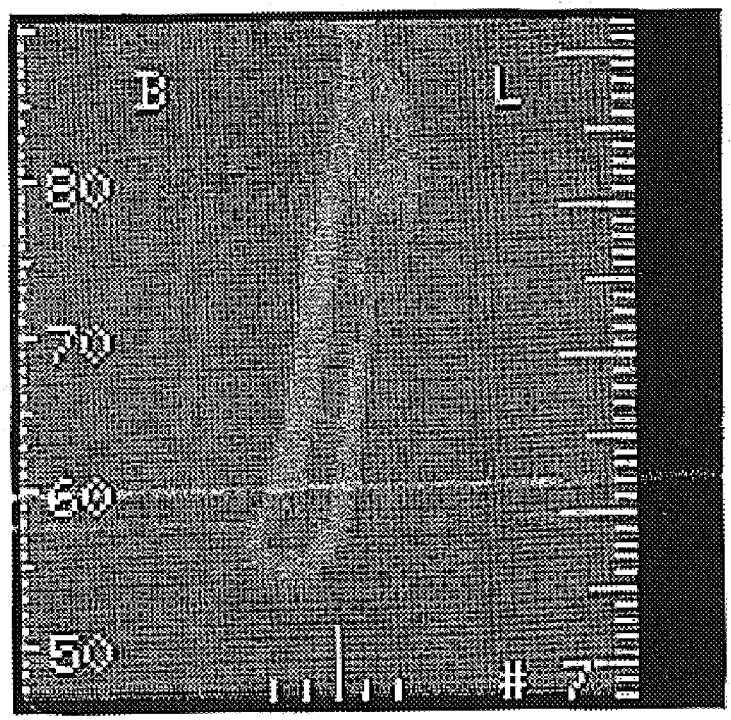
FIGS. 5A through 5I illustrate the images of CT slices from steps in the method of FIGS. 4A through 4D.

Referring to FIG. 3A, the mandible image is sliced in the axial direction of the backbone (from the top to the bottom of the mandible as shown in FIG. 3A), i.e., along lines A–A', B–B' and C–C' to form "intersections" of the mandible. It is referred to as the intersection image viewed from the direction indicated by the arrow 31 as a slice image. Here, the interval between intersections generally depends on the resolution of the CT image. As the interval becomes narrow, alveolar nerve regions can be detected more accurately. However, the processes to be described with reference to FIGS. 4A through 4D must be iterated as many times as the number of sliced intersections, so that the time required for identification of the alveolar nerve region increases. The obtained intersection images are provided as an "input image" as shown in FIG. 5A.

FIG. 3B shows a case where the mandible image is sliced perpendicular to the dashed central line 38 of the mandible, i.e., along lines A–A' and B–B' to obtain "intersections" of the mandible. Here, it is referred to the intersection image viewed from the directions indicated by the allows 35 or 36 as a slice image. The alveolar nerves are located along the central line of the mandible. Thus, if alveolar nerve regions are identified from each of the intersections cut in the direction as shown in FIG. 3B, and then combined into a complete alveolar nerve region, a result can be obtained which is more preferable than that produced by the slicing technique illustrated in FIG. 3A. However, although the alveolar nerve region is identified from the intersections cut in the parallel direction as shown in FIG. 3A, which are not perpendicular to the central line of the mandible, a distinctive difference is not shown between the results from the different slicing techniques, because the slicing interval is considerably narrow. Therefore, it can be concluded that slicing a mandible image as shown in FIG. 3A is simpler compared to the technique illustrated in FIG. 3B.

In the present embodiment, a 3-dimensional image of a mandible obtained by CT is sliced into a plurality of 2-dimensional slices as shown in FIGS. 3A or 3B, and the alveolar nerve region of the mandible for each of the slice images is identified by the method illustrated in FIGS. 4A through 4D. After the nerve region is detected from each slice image, the image of all slices is combined to form the complete alveolar nerve region of the mandible using the nerve regions of the slice images.

FIGS. 4A through 4D are flowcharts illustrating a method for identifying an alveolar nerve region in a mandible image according to the present invention. FIGS. 5A through 5I illustrate slice images obtained from steps of the method illustrated in FIGS. 4A through 4D.

In step 41, a mandible image is formed by CT and then sliced into 2-dimensional slices as described with reference to FIG. 3A or 3B. FIG. 5A shows the image of one of the slices, which will be referred to as "input image". The intensity of each pixel of the slice has a value between 0 to $2^N-1$, where N is the number of bits used to represent each pixel. If N=16, the maximum pixel intensity is 65,535.

In general, CT slice images are annotated with various computer-added texts, for example, the slice number, and the height and width of the slice. These annotations are located around the edge of the slice, and have a constant intensity, which is much higher than that of neighboring pixel intensities. In step 42, the pixels having the greatest intensities, which includes the pixels of the annotation information, are detected and then the intensity of the detected pixels is set to zero or the minimum value. In other words, after scanning all pixels of the slice image to find the maximum pixel intensity, the intensity of all of the pixels having the same or slightly low intensity as the maximum pixel intensity is set to zero (black).

Figure 5B:
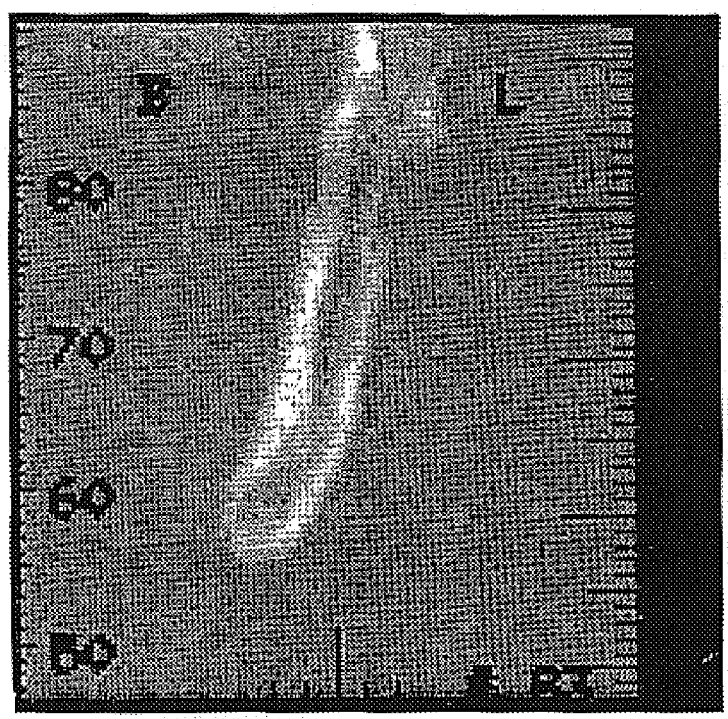

In the case where a patient has one or more teeth treated with amalgam, such artificial structures absorb X-rays and appear to be very bright in the CT slice image, and are commonly located at the upper part of the mandible image. Thus, there is a need to set the intensity of these pixels, which belong to such bright regions, to zero or the minimum pixel intensity. In particular, the centroid and the uppermost coordinates of the mandible object are calculated and the mean intensity of the pixels between the two coordinates is calculated. Then, the intensity of the pixels having a greater intensity than the mean pixel intensity is set to zero. FIG. 5B shows the slice image after step 42, from which the pixels for the annotations and artificial structure are removed.

Figure 5C:
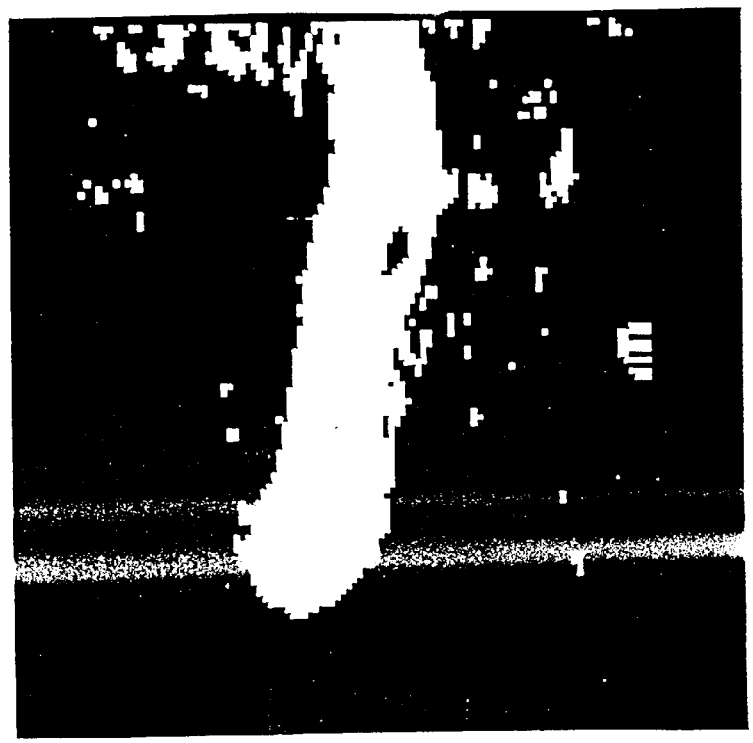

Then, a binary image (consisting of "0"s and "1"s) for the mandible region is approximately separated from the input image from which the annotation information was removed, which is referred to as a mandible object. The mean intensity of the mandible object is greater than that of the background region, and thus a predetermined threshold value is set to eliminate the pixels having a smaller intensity than the threshold value, such that the mandible region can be distinguished from the other regions. If the pixel intensity is greater than the threshold value, the pixel intensity is set to 1 (white). Otherwise, if the pixel intensity is less than the threshold value, the pixel intensity is set to 0 (black). As a result, a binary image as shown in FIG. 5C is obtained, which is so-called a mandible object (step 43). The mean pixel intensity of the CT slices can be set as the threshold value.

However, when the binary image is obtained using a threshold value, as shown in FIG. 5C, many unnecessary smaller objects in addition to the mandible object may appear. For this case, the threshold value is multiplied by a predetermined coefficient, for example, "Mean_Multiplier", to reduce the occurrence of such unnecessary objects. In step 42, the intensity of the annotation pixels is set to zero, so that the mean intensity of all pixels is lowered. Thus, the amount of annotation must be regarded in determining the coefficient "Mean_Multiplier". Results of experimentation by the inventor indicate it is preferable that the coefficient has a value of about 1.25.

Figure 5D:
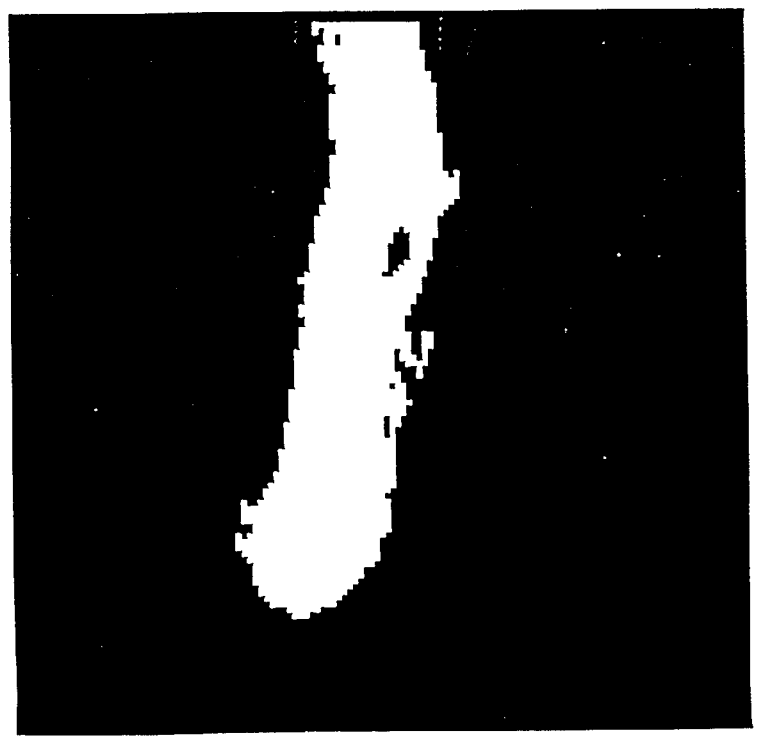

The mandible objects shown in FIG. 5C, which are determined in step 43 using a threshold value, may include the mandible region and the non-mandible region. Usually, the binary object corresponding to the mandible region is the largest, and thus the largest object is considered to be the mandible region. Thus, in step 44, the largest binary object is screened as the mandible object. In other words, the size of all of the objects in the image is compared, and the pixels of the largest object are set to "1" while the remaining pixels are set to "0", to determine the mandible object. The image of the mandible object is shown in FIG. 5D.

Figure 5E:
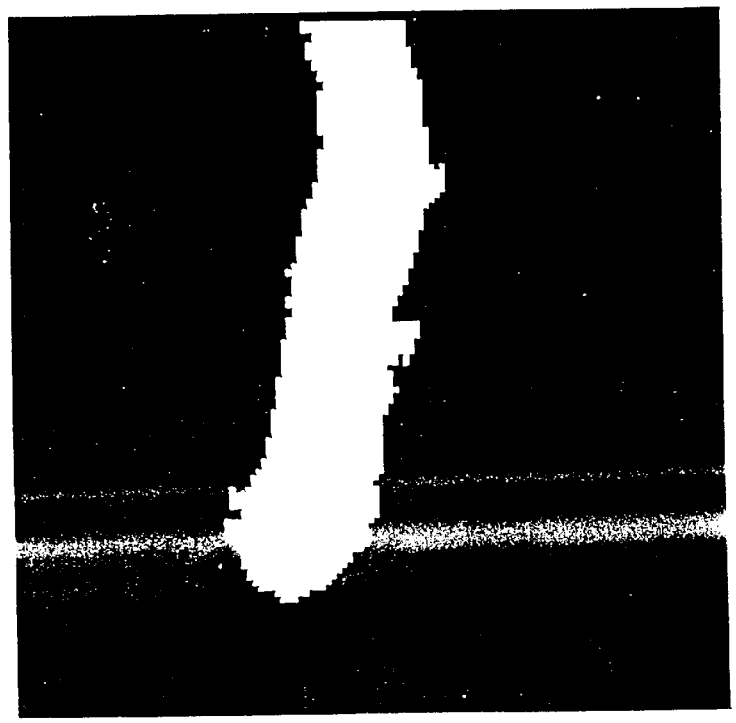

Many cavities are present in the binary mandible object, because the density of mandible is not uniform over the entire region. In other words, the hard edge of the mandible has a high density, whereas the marrow or fatty tissue, which is surrounded by the hard edge, has a relatively low density. For obtaining the largest contiguous object, a closing operation is performed to eliminate the small cavities from the mandible object (step 45). Then, an erosion operation may be performed with respect to the binary object image to smooth the edge of the binary object. FIG. 5E illustrates the binary image of the mandible object obtained from step 45, which is called a "bm image".

Then, a contrast enhancement technique is applied to the mandible object of the original "input image" (see FIG. 5A) in step 46. The intensity range of the mandible image, and particularly, the intensity range of nerves and osseous structure of the mandible is not clearly known yet. However, the intensity ranges of the osseous region and alveolar nerve region can be approximately determined by applying the contrast enhancement technique to the mandible object.

Figure 5F:

First, for the intensity range of the mandible region, the pixels for the mandible regions corresponding to the binary mandible object of FIG. 5E are extracted from the "input image" of FIG. 5A. Then, the maximum pixel intensity of the extracted pixels is set as "MAX" and the minimum pixel intensity is set as "MIN". For a contrast-enhanced image, a contrast-enhanced intensity is computed for each pixel belonging to the mandible object, using the formula (1). FIG. 5F shows the image of the contrast-enhanced mandible object.

$$\text{ENH\_DEN} = (\text{Max\_T} - \text{Min\_T}) * \frac{\text{PIX DEN} - \text{MIN}}{\text{MA} - \text{MIN}} + \text{Min\_T} \quad (1)$$

In the formula (1), ENH_DEN represents the intensity of a contrast-enhanced pixel, Max_T represents the maximum pixel intensity for the mandible object, Min_T represents the minimum pixel intensity for the mandible object, and PIX_DEN represents the intensity of the original pixel before the contrast enhancement.

After the contrast-enhancement with respect to the input image corresponding to the mandible object, the pixels belonging to the mandible object are subjected to the K-means clustering algorithm to obtain a plurality of clusters each containing pixels having a similar pixel intensity (step 47). The mean pixel intensities for the clusters may be set to 0, $10 \times 10^3$, $15 \times 10^3$, $20 \times 10^3$, $25 \times 10^3$, $45 \times 10^3$ and $500 \times 10^3$. Each of the pixels is assigned to one of the 7 clusters based on its intensity.

Figure 5G:
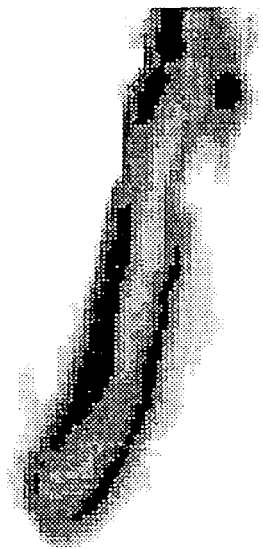

The cluster having the maximum mean intensity includes pixels having a higher intensity, which may be caused by an artificial metal implant, and the cluster having the relatively low mean intensity includes pixels for the background and nerve tissues. Also, the clusters having medium mean intensities include pixels for the hard osseous structure and the canal surrounding alveolar nerves. After grouping the pixels of the image into clusters, alveolar nerve regions are detected later based on the clusters. FIG. 5G shows the 7-level cluster image with respect to the mandible object, which is obtained by applying the K-means clustering algorithm based on pixel intensities and referred to as a "cluster image".

Hereinafter, a step of obtaining candidate alveolar nerve pixels from the "cluster image" and "bm image" will be described.

After all of the pixels for the mandible object are assigned to one of the clusters, for finding candidate alveolar nerve object which is highly likely to be the alveolar nerve region, clusters that contain more pixels than a predetermined minimum number of pixels, for example, more than 10 pixels, are determined, and then the cluster having the lowest cluster number, i.e., the cluster having the lowest mean intensity, is defined as "K_Min". In other words, for the cluster containing candidate alveolar nerve pixels, at least 10 pixels must be contained in the cluster and the cluster number must be as low as possible. This is because the alveolar nerve pixels are known to have a low intensity and the low intensity pixels belong to a cluster labeled with a lower number.

Then, the pixels of the clusters labeled with a number of "K_Min" or less among the pixels, which are already set to "1" (mandible regions), of the binary image "bm image", are set to "1", and the other pixels are set to "0", to produce a new binary image (step 48).

Figure 5H:
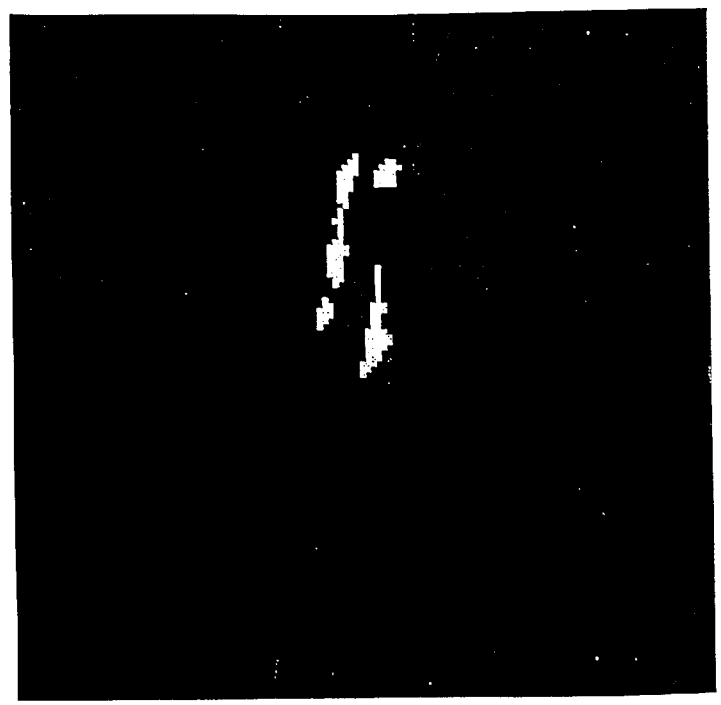

A plurality of objects, which are contained in the binary image obtained from step 48, are sequentially labeled with numbers starting from "1". Also, objects containing few pixels are regarded as noise components and, thus, must be removed from the image. Thus, the pixels of objects having a minimum number of pixels, "Min_Number", are set to "0" and then removed (step 49). Preferably, "Min_number" is 5. After removing the small objects using the value "Min_Number", the remaining "candidate" alveolar nerve objects are relabeled and subjected to the following processes. FIG. 5H shows the candidate alveolar nerve objects after step 49 is completed.

After step 49, usually there remains one or more candidate alveolar nerve objects. Thus, the most probable candidate alveolar nerve object is selected based on the following characteristics of the alveolar nerve. The intensity of alveolar nerve region is slightly lower than that of the perimeter, which is the canal region surrounding the alveolar nerve region. The alveolar nerve region of the mandible is expressed as a circular dark region (having a lower intensity), which is surrounded by an annular canal region consisting of pixels having a slightly higher intensity compared to the alveolar nerve region. Also, the canal region is surrounded by a white bone region (having a much higher intensity). Thus, for the most probable candidate alveolar nerve object, the intensity of the perimeter of the candidate alveolar nerve object must be slightly higher than that of the inner nerve region thereof.

In step 50, the intensities of the inner pixels of the candidate objects are compared with those of the pixels of the perimeter region of the object to determine whether the candidate alveolar nerve object correspond to the real, alveolar nerve region. This step will now be described in greater detail with reference to FIG. 4B.

In order to determine a cluster number with respect to the perimeter pixels of the candidate nerve objects, the binary objects of FIG. 5H are subjected to a morphological dilation operation to extract the perimeter regions thereof (step 502). The perimeter region of each object forms a narrow annular region. To determine whether the annular region corresponds to the canal surrounding the alveolar nerve of the mandible, cluster numbers with respect to the perimeter pixels within the annular regions must be calculated.

For the most probable candidate alveolar nerve object, the cluster number of the perimeter pixels, which constitute the annular region surrounding the candidate nerve object, must be slightly larger than that of the inner pixels of the candidate nerve object surrounded by the annular canal region.

Thus, the number ($P_1$) of perimeter pixels, and the number ($P_2$) of pixels for the cluster labeled with "K_Min+1" or "K_Min+2" among the perimeter pixels are counted (step 504). In order to determine whether the candidate nerve object has perimeter pixels that have a slightly higher intensity than the inner pixels surrounded by the same, the percentage of the pixels contained in the cluster "K_Min+1" or "K_Min+2" with respect to the perimeter pixels is calculated (step 506). If the calculated percentage is less than, for example, 80%, which may be considered not to meet the characteristics of the alveolar nerves, the candidate nerve object is removed from the binary image (step 508).

Figure 5I:
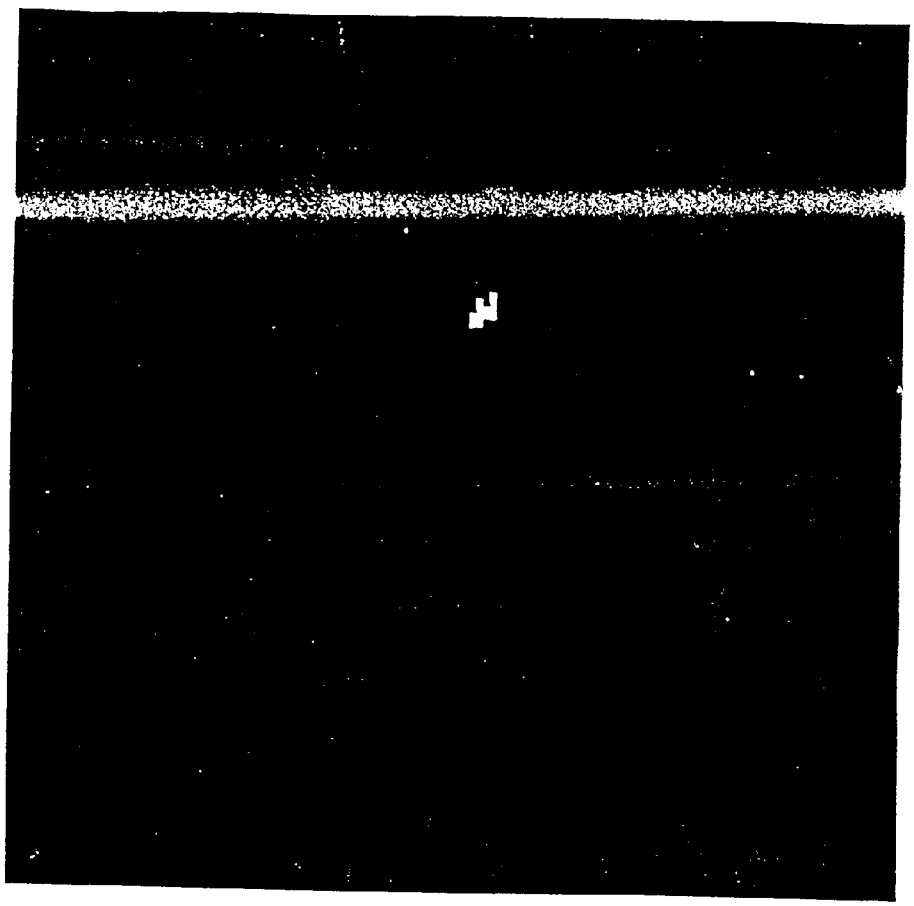

The steps 502 through 508 are repeated with respect to all of the candidate nerve objects to screen more possible candidate objects. FIG. 5I shows an example of the binary image of the most probable candidate nerve object obtained using the above steps.

Next, in step 51, from the remaining candidate nerve objects, the objects corresponding to regions that are considered to be fatty marrow tissues in the mandible, beside the alveolar nerve region, are removed. A feature of object containing only fatty marrow tissues is that the object is surrounded by a number of pixels having an almost same intensity. Thus, candidate objects associated with marrow tissues can be eliminated by comparing the pixel intensity of the object with that of neighboring pixels of the object. Step 51 will now be described with reference to FIG. 4C.

First, the number of pixels of the candidate nerve object is counted and defined as $N_1$ (step 511). Then, the centroid point of the candidate nerve object is calculated and determined as a "seed" point (step 512). Then, a region growing algorithm is applied starting from the seed point (step 513). Here, the cutoff value for the region growing process is set to 0.085, and the region growing from the seed point is continued until all pixels having a predetermined intensity range are included in a grown region. In other words, if the intensity of a neighboring pixel of the grown region is within 8.5% of the mean intensity of all pixels of the grown region, the neighboring pixel is incorporated into the grown region. After the region growing is completed, the number of the pixels of the grown nerve object is counted and defined as $N_2$ (step 514).

Then, the number ($N_1$) of pixels of the original candidate nerve object and the number ($N_2$) of pixels within the grown nerve object are compared (step 515). In particular, if $N_2$ is much greater than $N_1$, it is highly possible that the candidate nerve object is a marrow tissue region rather than the alveolar nerve region. If $N_2$ is about 3 times greater than $N_1$, the probability that the candidate nerve object is the alveolar nerve region is very low, and thus the candidate nerve object is removed from the image (step 516). The steps 511 through 516 are repeated for all of the candidate objects and the process goes to step 52.

In step 52, it is determined whether the candidate nerve object is spatially adjacent to the edge of the mandible region. Alveolar nerves are generally located at the edge of the mandible region, and particularly, at the area where alveolar nerves enter the mandible. Thus, if it is confirmed that the candidate nerve object contacts the edge of the mandible (step 53), the candidate nerve object is determined to be a real alveolar nerve region and then the process is terminated. Otherwise, the process is followed by subsequent steps.

For the determination of whether the candidate nerve object contacts the edge of the mandible region, first the candidate nerve object is subjected to a morphological dilation operation and then it is checked whether the candidate nerve object that has undergone the dilation operation extends to the edge of the mandible region. If so, it means that the original candidate nerve object before the dilation contacts the edge of the mandible region, and thus it is highly possible that the candidate nerve object is a real alveolar nerve region.

Next, in step 54, it is determined whether the candidate nerve object is the alveolar nerve region based on which area of the mandible region the CT slice is taken from. The intersection of the mandible of a patient varies. That is, the upper and lower parts of the mandible intersection have the same width, or the upper part of the mandible is wider than the lower part thereof. In view of anatomy, the position of the alveolar nerves is determined relative to the shape of the mandible intersection. In other words, the area of the mandible from which the CT slice is taken must be concerned in the determination of whether the candidate nerve object corresponds to an alveolar nerve region. Step 54 will now be described with reference to FIG. 4D.

First, a centroid point with respect to all of the pixels of the mandible image of a CT slice is calculated (step 541). The uppermost and lowermost pixels of the mandible region are determined, and a halfway point between the two pixels is calculated (step 542). Then, it is determined whether the centroid point is close to the halfway point (step 543). If the centroid point is located near the halfway point, which means that the mandible intersection has a similar width at the upper and lower parts, the process moves to step 545. Otherwise, step 544 is performed. In step 543, preferably, when the distance between the centroid point and the halfway point is within a predetermined percentage of the distance between the uppermost and lowermost pixels, for example, within 10% thereof, the centroid point is determined to be close to the halfway point.

Step 545 is performed in the case where the width of the mandible region is nearly constant from the top to the bottom. It is known from experiment results that alveolar nerves are located above the halfway point and close to the centroid point. Thus, in step 545, it is determined whether a candidate nerve object is located above the halfway point. If such candidate nerve objects exist in the image, the candidate nerve object nearest to the centroid point is selected and determined to be a real alveolar nerve region. Also, if no candidate nerve objects are located above the halfway point, the candidate nerve object below the centroid point that is the nearest to the centroid point, is selected and determined to be a real alveolar nerve region (step 547).

Meanwhile, step 544 is performed in the case where the width of the mandible region is not constant in the vertical direction, as described previously. In step 544, the candidate nerve object that is the nearest to the centroid point is selected and determined to be a real alveolar nerve region.

The most probable candidate alveolar nerve object is obtained for one CT slice image of the mandible through the above processes. The above steps, from steps 42 through 54, are repeated with respect to all of the CT slices from the mandible image to produce a candidate nerve object fir each slice image. Then, the most possible candidate alveolar nerve objects from each CT slice image are rendered to produce a complete alveolar nerve image.

FIG. 6 is a flowchart illustrating another method for identifying an alveolar nerve region in a mandible image according to the present invention. FIGS. 7A through 7E show the images obtained from the processes by the method illustrated in FIG. 6. Compared to the method described with reference to FIGS. 4A through 4D, in which a series of steps for identification of the alveolar nerve region are automated, the method of FIG. 6 may be categorized as a kind of semi-automated process because a seed point with respect to each CT slice image of the mandible image is manually chosen by a user. In other words, a user (dental surgeon) indicates a region or a point of a CT slice image that is considered to be the alveolar nerve region, and a region growing algorithm is applied using the region indicated by the user as a seed point, to identify an alveolar nerve region within the CT slice image of the mandible. The selection of the seed point by the user based on experience allows the omission of a series of time consuming steps performed in the method, which was described with reference to FIGS. 4A through 4D, to obtain candidate nerve objects, which saves much time. Thus, the image processing speed can be improved.

According to the alveolar nerve identification method described with reference to FIGS. 4A. through 4D, candidate nerve objects are determined from all of the CT slices and rendered into a complete alveolar nerve image. Compared to the method of FIGS. 4A through 4D, the alveolar nerve identification method of FIG. 6 detects an alveolar nerve region from one CT slice image of a mandible based on the indicated seed point, and performs a region growing process from the detected nerve region with respect to a neighboring CT slice to produce an alveolar nerve image. By doing so, the overall processing speed can be sharply improved. The method of FIG. 6, in which the alveolar nerve image is produced by the region growing with respect to neighboring CT slices, can be applied to the method of FIGS. 4A through 4D. For example, after the most probable candidate nerve object is detected from one CT slice image of a mandible, the same region growing process as in FIG. 6 can be applied with respect to neighboring CT slices based on the most probable candidate nerve object of the previous slice image.

Referring to FIG. 6, first one CT slice $S_i$ is taken from a mandible image (step 61). A 3-dimensional mandible image is sliced into 2-dimensional slice images using the technique of FIG. 3A or 3B, and one of the 2-dimensional slice images is selected. Then, as in step 42 of FIG. 4A, annotations are removed from the slice image, and an image processing technique, such as contrast enhancement, is applied to the slice image to show the image of the mandible region on a display screen.

In the present embodiment, one of the pixels belonging to the slice image is determined to be a seed point, and the region growing is performed starting from the seed point with respect to the slice image. For easy understanding of the region growing process, the characteristics of alveolar nerves are briefly described as follows.

(1) Alveolar nerves are surrounded by the canal, which forms a continuous tubular shape, and are not branched.

(2) Alveolar nerves continuously extend in the mandible.

(3) Cross sections of alveolar nerves have an almost same area.

(4) An alveolar nerve region inevitably overlaps between neighboring CT slices.

(5) The pixel intensity of the alveolar nerve region in the CT image is within a certain range, for example, 1100 to 1700.

(6) The pixel intensity of the alveolar nerve region is within a predetermined error range.

(7) Commonly, the alveolar nerve region obtained from one 2-dimensional CT slice image is expressed as a closed figure. Only the two alveolar regions of the mandible, where the nerves enter the mandible and go out of the same, are shown as open figures in a CT slice image.

In step 62, candidate nerve pixels in the CT slice image, which would be a seed point for a region growing process to be performed to obtain an alveolar nerve region, are displayed on a screen. Because the pixel intensity of pixels corresponding to an alveolar nerve region is in the range of 1100 to 1700, such pixels having a pixel intensity within the range are displayed as candidate nerve pixels. Then, a user indicates one of the candidate nerve pixels as the seed point (step 63).

Figure 7A:
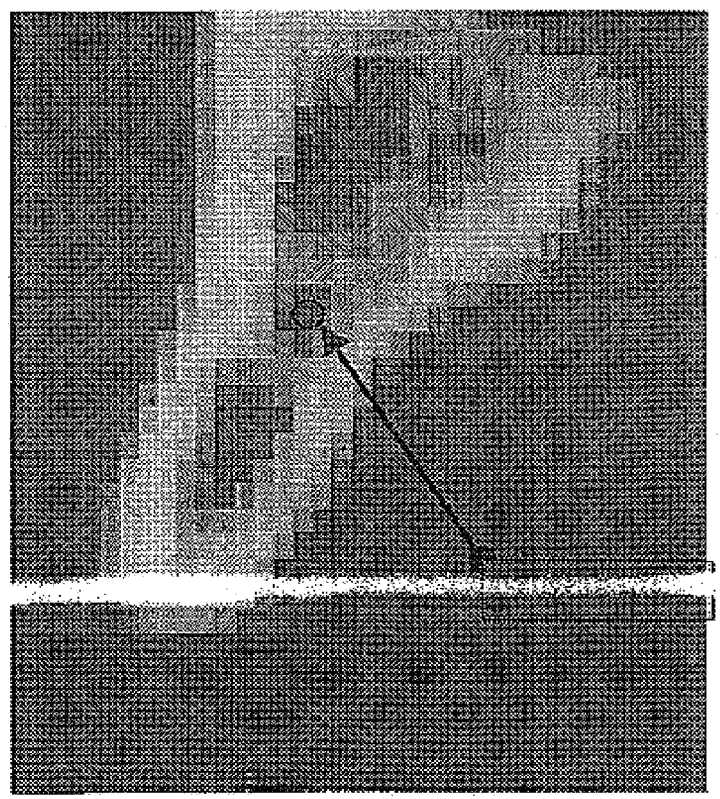
FIGS. 7A through 7E illustrate the images of CT slices from steps in the method of FIG. 6.

FIG. 7A shows an example of a seed point selected by a user in a CT slice image. It is not difficult for a dental surgeon to find an alveolar nerve region in a CT slice image based on experience.

Figure 7B:
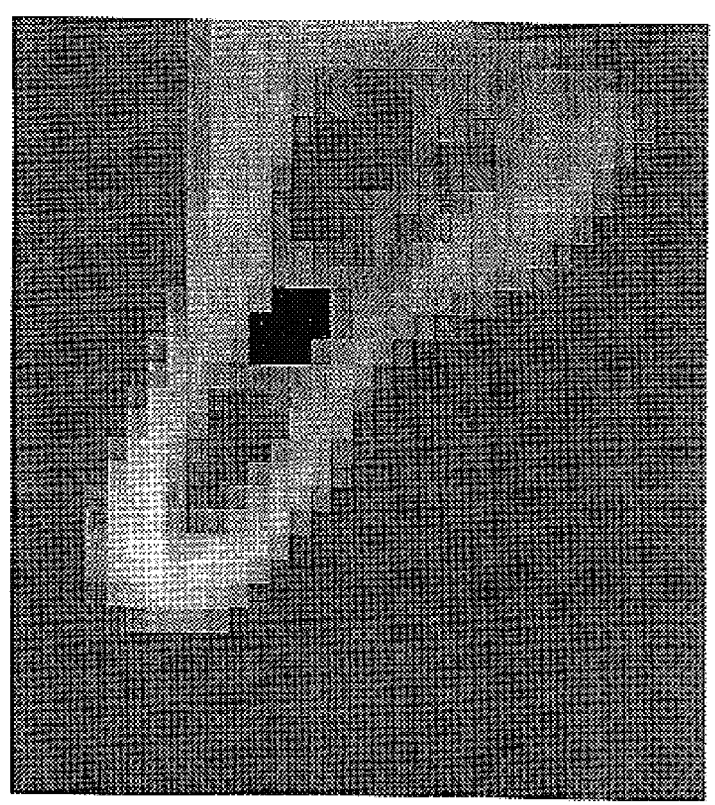

Based on the characteristics of alveolar nerves mentioned previously, a region growing process is performed with respect to neighboring pixels from the seed point to obtain an alveolar nerve region for the slice image (step 64). The region growing process is performed as follows. First, the pixel intensity of the seed point is compared with that of a neighboring pixel, to determine whether the difference between the two pixel intensity values is within an error range d, which is expressed by the formula (2) hereinbelow. If the pixel intensity of the neighboring pixel is within the error range, the pixel is determined to be a part of the alveolar nerve region. FIG. 7B shows an alveolar nerve region grown from the seed point of a CT slice image. In FIG. 7B, the dark area indicates the grown nerve region.

$$d = (DV_{max} - DV_{min}) * 0.05 \qquad (2)$$

In the formula (2), $DV_{max}$ and $DV_{min}$ represent the maximum and minimum pixel density values, respectively, in the mandible region. The coefficient, 0.05, can be appropriately varied depending on the resolution of CT slice images.

After the pixels corresponding to the alveolar nerve region are identified from one CT slice $S_i$, the region growing process is applied to neighboring CT slice $S_{i-1}$ or $S_{i+1}$, which is located before or after the CT slice $S_i$, based on the nerve region of the CT slice $S_i$, to expand the nerve region of the slice $S_i$ toward the neighboring CT slices $S_{i-1}$ and $S_{i+1}$ (steps 65 through 67).

In particular, in step 65, an 8-neighboring pixel region is set as a template region based on the alveolar nerve region of the CT slice $S_i$, which includes the obtained nerve region and each 8-neighboring pixel for all pixels belonging to the nerve region. An alveolar nerve region is grown with respect to a neighboring slice $S_{i-1}$ or $S_{i+1}$, which is located before or after the CT slice $S_i$, so as not to extend beyond the template region obtained from the CT slice $S_i$.

Figure 7C:
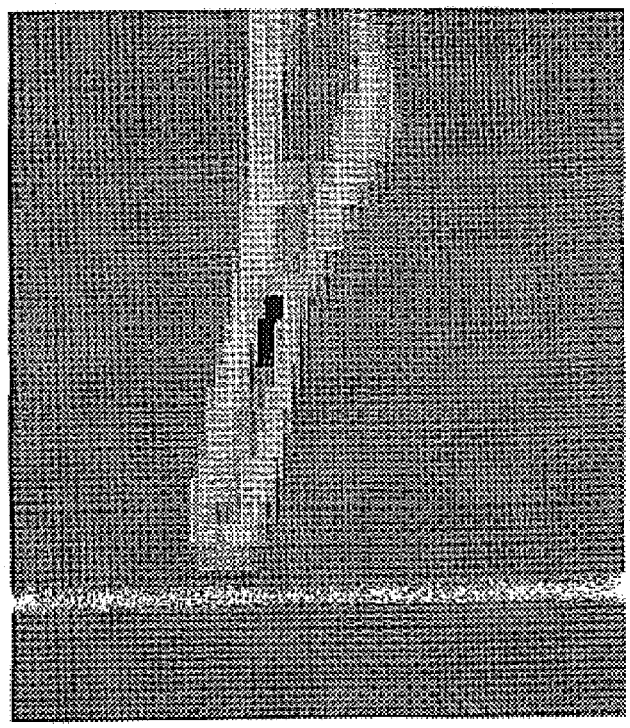
Figure 7D:
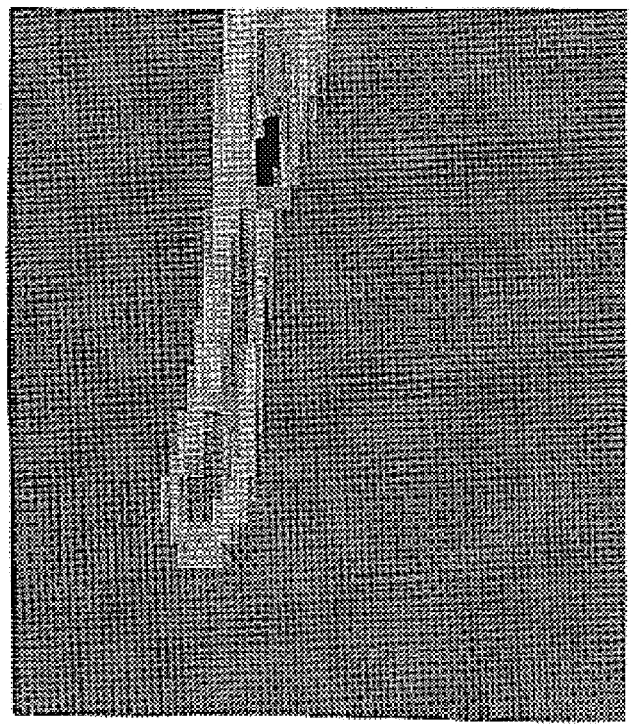

In step 66, a pixel having the lowest pixel intensity among pixels belonging to a region of the neighboring slice $S_{-1}$ or $S_{i+1}$, corresponding to the template region, is determined to be a seed point for region growing with respect to the neighboring slice $S_{i-1}$ or $S_{i+1}$. The reason why the lowest intensity pixel is determined to be the seed point is that the inner region of alveolar nerve has a relatively smaller density than the canal thereof. Then, the region growing is performed with respect to the CT slice $S_{i-1}$ or $S_{i+1}$ from the seed point in the same manner as in step 64 to obtain an alveolar nerve region of the slice $S_{i-1}$ or $S_{i+1}$ (step 67). FIG. 7C shows a case where the alveolar nerve region is located near the halfway point of the mandible, and FIG. 7D shows a case where the alveolar nerve region is located near the top of the mandible.

The previously mentioned steps are performed with respect to all CT slices (step 68), and the alveolar nerve regions obtained from all CT slices are rendered into a complete alveolar nerve region of the mandible (step 69).

Figure 7E:
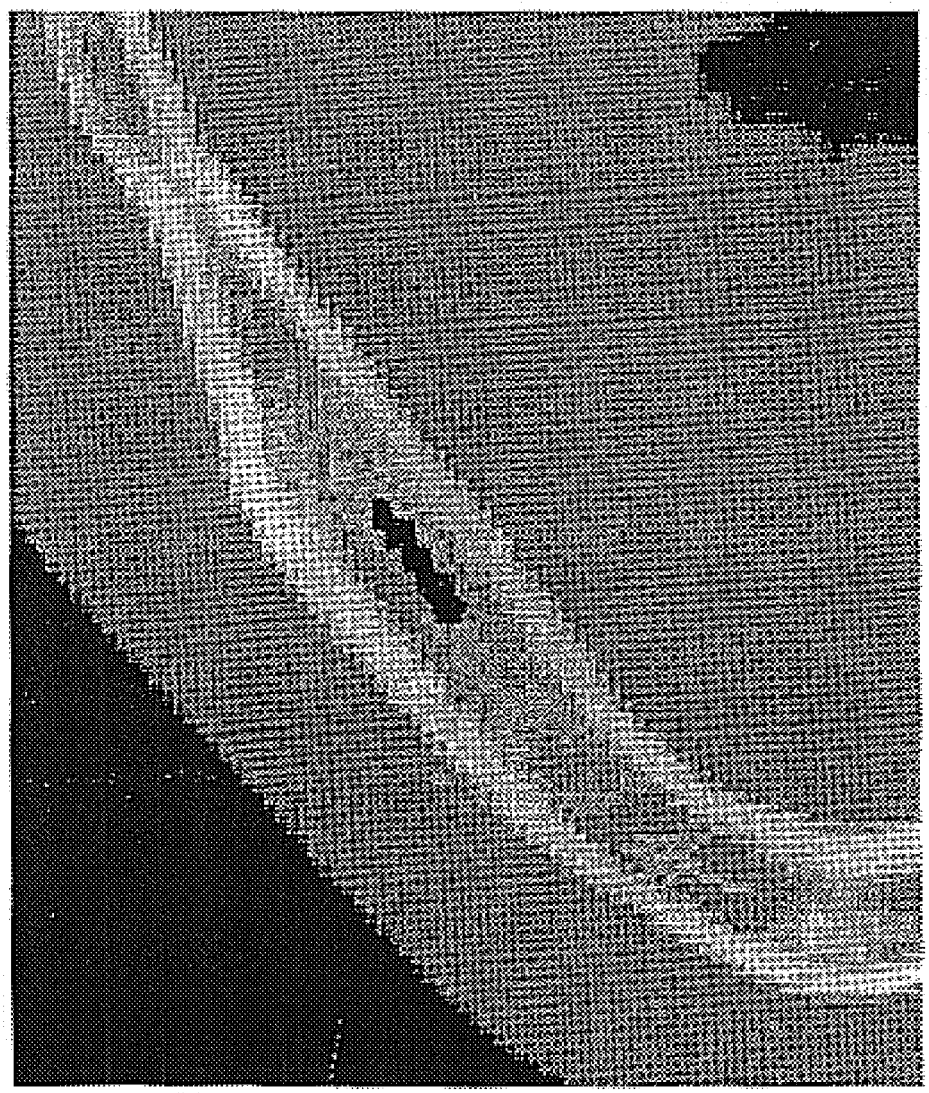

FIG. 7E is a cross section of the mandible image taken along the halfway line of the mandible image, which shows the alveolar nerve region detected through the previously mentioned steps. A dental surgeon can identify the alveolar nerve region in the mandible image of a patient through the above mentioned method, which allows the dental surgeon before implantation to simulate whether or not an implant screw may encroach on the alveolar nerves.

Figure 8:
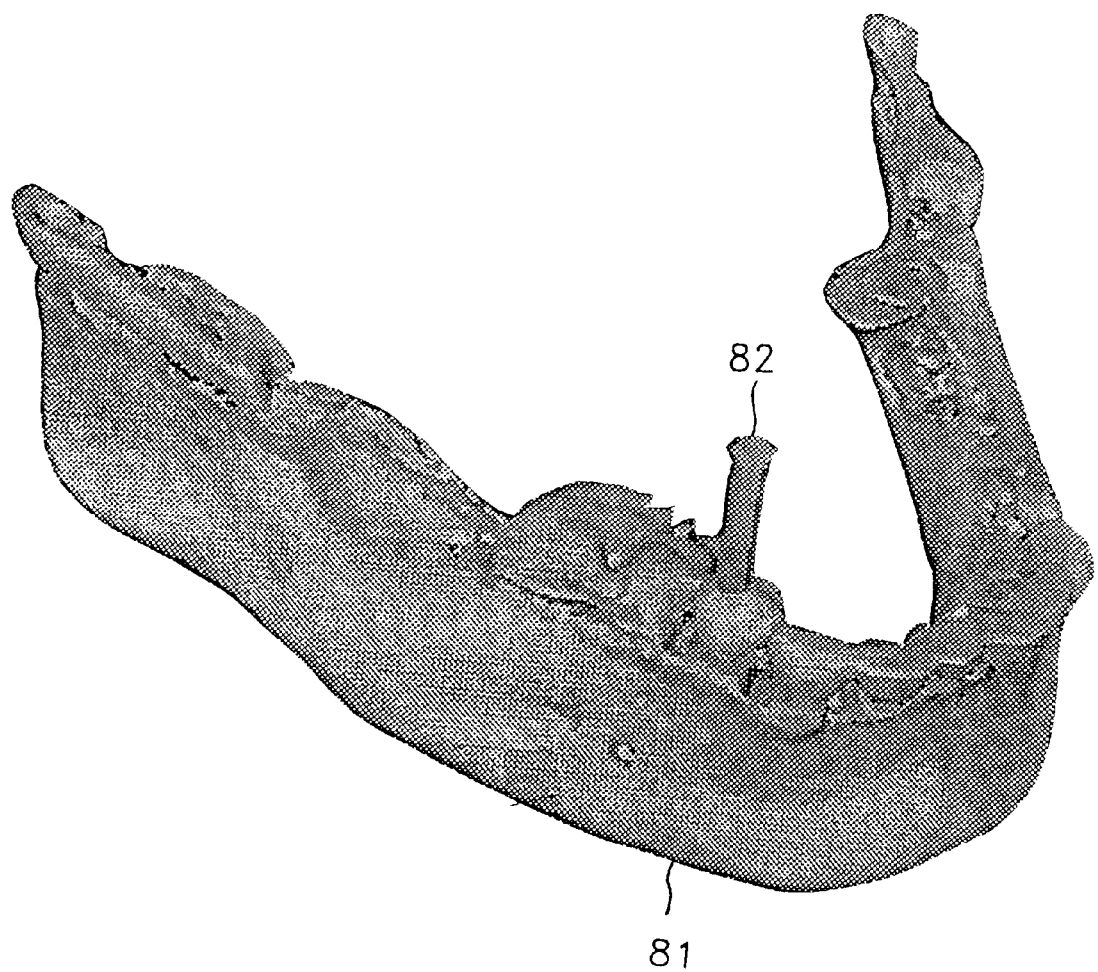
FIG. 8 illustrates a state where a virtual screw implant is inserted into an implant site of a mandible image.

FIG. 8 shows a state where an implant screw is inserted into an implant site of the mandible image of a patient, which illustrates simulation for the implantation. In FIG. 8, reference numeral 81 represents a 3-dimensional mandible image, and reference numeral 82 represents a virtual implant screw.

For the simulation of implantation, the virtual implant screw is inserted into the implant site of the mandible image to determine the pixels which contact the inserted virtual implant screw. Then, it is determined whether the screw contacts pixels belonging to the alveolar nerve region detected by the inventive method. That is, a dental surgeon can arbitrarily determine the location, orientation and depth of the virtual implant screw, such that the implant screw does not contact the alveolar nerves, which allows for safe implantation.

The invention can also be embodied as computer readable code on a computer readable medium. The computer readable medium is any data storage device that can store data which can thereafter be read by a computer system. Examples of the computer readable medium include read-only memories, random-access memories, CD-ROMs, magnetic tapes, floppy disks and optical data storage devices. The computer readable medium can also be distributed over network coupled computer systems so that the computer readable code is stored and executed in a distributed fashion.

As described above, the method of identifying an alveolar nerve region in a mandible image according to the present invention allows a dental surgeon to accurately detect the alveolar nerve region for safe implantation in an automated manner. Also, a potential alveolar nerve region, which is determined by a dental surgeon based on his or her experience with CT imaging, is confirmed by comparison with the alveolar nerve region determined by the inventive method, and thus an actual implantation can be much more carefully carried out.

As previously mentioned in an embodiment of the present invention, a seed point, which is the starting point for region growing for alveolar nerve identification, can be personally determined by a user (dental surgeon), and can be used as the basis for region growing within one CT slice or between neighboring CT slices to identify an alveolar nerve region, thereby improving the nerve detection speed.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method of identifying an alveolar nerve region in a mandible image, comprising the steps of:
   (a) slicing a 3-dimensional mandible image into a number of 2-dimensional slice images;
   (b) detecting a binary image object corresponding to a mandible region from one of the slice images;
   (c) grouping pixels of the binary image object of the mandible region into clusters each containing pixels having a similar intensity;
   (d) determining clusters that have more than a predetermined minimum number of pixels, and determining a minimum labeled cluster having the lowest pixel intensity distribution among the clusters;
   (e) composing a new binary image containing pixels which belong to both the mandible region and the clusters having intensity distribution lower than or equal to that of the minimum labeled cluster, to extract a candidate nerve object; and
   (f) determining whether the candidate nerve object corresponds to the alveolar nerve region.

2. The method of claim 1, further comprising (g) determining candidate nerve objects for the real alveolar nerve region with respect to all of the slice images, and assembling all of the slice images into a mandible image to produce a complete alveolar nerve region in the mandible image using the candidate nerve objects.

3. The method of claim 1, further comprising (g) identifying an alveolar nerve region for a neighboring slice image $S_{i-1}$ or $S_{i+1}$, which is located before or after the slice image $S_i$ by growing the alveolar nerve region determined from the slice $S_i$.

4. The method of claim 1, wherein step (a) further comprises removing pixels corresponding to annotation information and an artificial structure from the slice image.

5. The method of claim 1, wherein in step (b) the mean intensity value of all of the pixels in the slice image, or a predetermined threshold value obtained by multiplying the mean intensity value by a predetermined coefficient, is compared with the intensity of each of the pixels belonging to the slice image, and the binary image object corresponding to the mandible region is formed based on the comparison result.

6. The method of claim 1, after step (b) further comprising enhancing contrast by interpolating the intensity of each pixel using maximum and minimum pixel intensity values for the pixels corresponding to the mandible region of the slice image.

7. The method of claim 1, wherein step (f) comprises:
   (f1) performing a dialation operation on the candidate nerve object to extract the perimeter region thereof;
   (f2) comparing the intensity of the pixels belonging to the perimeter region with the intensity of the inner pixels surrounded by the perimeter region; and
   (f3) determining an object having a perimeter region whose pixel intensity is greater than that of the inner pixels, as a new candidate nerve object.

8. The method of claim 1, wherein step (f) comprises:
   (f1) calculating the number $N_1$ of pixels belonging to the candidate nerve object;
   (f2) calculating the centroid point of the candidate nerve object;
   (f3) performing a region growing operation on the candidate nerve object, starting from the centroid point as a seed point to produce a grown nerve object;
   (f4) calculating the number $N_2$ of pixels of the grown nerve object; and
   (f5) comparing $N_1$ and $N_2$, and if $N_2$ is greater than $N_1$ by a predetermined number or more, removing the candidate nerve object.

9. The method of claim 1, wherein step (f) comprises:
   (f1) calculating a centroid point with respect to all of the pixels belonging to the mandible region of the slice image;
   (f2) determining the uppermost and lowermost pixels of the mandible region, and calculating a halfway point between the uppermost and lowermost pixels;
   (f3) determining whether the centroid point is located near the halfway point; and (f4) if the centroid point is located near the halfway point, determining the candidate nerve object above the halfway point and nearest to the centroid point, or the candidate nerve object below and nearest to the centroid point, to be a real alveolar nerve region, and if the centroid point is not near the halfway point, determining the candidate nerve object nearest to the centroid point to be an alveolar nerve region.

10. A computer readable medium having embodied thereon a computer program for identifying an alveolar nerve region in a mandible image, wherein the alveolar nerve region identification comprises the steps of:
   (a) slicing the 3-dimensional mandible image into a number of 2-dimensional slice images;
   (b) detecting a binary image object corresponding to a mandible region from one of the slice images;
   (c) grouping pixels of the binary image object of the mandible region into clusters each containing pixels having a similar intensity;
   (d) determining clusters that have pixels more than a predetermined minimum number of pixels, and determining the minimum labeled cluster having the lowest pixel intensity distribution among the clusters;
   (e) composing a new binary image containing pixels which belong to both the mandible region and the clusters having intensity distribution lower than or equal to that of the minimum labeled cluster, to extract a candidate nerve object; and
   (f) determining whether the candidate nerve object corresponds to the alveolar nerve region.

11. A method of identifying an alveolar nerve region in a bone image, comprising:
   (a) obtaining a two-dimensional slice image of a bone;
   (b) detecting a binary image object corresponding to a bone region from one of the slice images;
   (c) grouping pixels of the binary image object of the bone region into clusters, each containing pixels having a similar intensity;
   (d) determining clusters that have more than a predetermined minimum number of pixels, and determining a minimum labeled cluster having the lowest pixel intensity distribution among the clusters; and
   (e) creating a new binary image containing pixels that belong to both the bone region and the clusters having intensity distribution lower than or equal to that of the minimum labeled cluster, to extract a candidate nerve object.

12. The method of claim 11, further comprising (f) determining whether the candidate nerve object corresponds to the alveolar nerve region.

13. The method of claim 11, wherein the bone is a mandible.

14. The method of claim 11, wherein the bone is a maxilla.

15. The method of claim 11, further comprising determining candidate nerve objects for the real alveolar nerve region with respect to all of the slice images, and assembling all of the slice images into a bone image to produce a complete alveolar nerve region in the bone image using the candidate nerve objects.

16. The method of claim 11, further comprising identifying an alveolar nerve region for a neighboring slice image $S_{i-1}$ or $S_{i+1}$, which is located before or after the slice image $S_i$, by growing the alveolar nerve region determined from the slice $S_i$.

17. The method of claim 11, wherein step (a) further comprising removing pixels corresponding to annotation information and an artificial structure from the slice image.

18. The method of claim 11, wherein in step (b) the mean intensity value of all of the pixels in the slice image, or a predetermined threshold value obtained by multiplying the mean intensity value by a predetermined coefficient, is compared with the intensity of each of the pixels belonging to the slice image, and the binary image object corresponding to the bone region is formed based on the comparison result.

19. The method of claim 11, after step (b) further comprising enhancing contrast by interpolating the intensity of each pixel using maximum and minimum pixel intensity values for the pixels corresponding to the bone region of the slice image.

20. The method of claim 11, wherein step (f) comprises:
   performing a dilation operation on the candidate nerve object to extract the perimeter region thereof;
   comparing the intensity of the pixels belonging to the perimeter region with the intensity of the inner pixels surrounded by the perimeter region; and
   determining an object having a perimeter region whose pixel intensity is greater than that of the inner pixels, as a new candidate nerve object.

21. The method of claim 12, wherein step (f) comprises:
   calculating the number $N_1$ of pixels belonging to the candidate nerve object;
   calculating the centroid point of the candidate nerve object;
   performing a region growing operation on the candidate nerve object, starting from the centroid point as a seed point to produce a grown nerve object;
   calculating the number $N_2$ of pixels of the grown nerve object; and
   comparing $N_1$ and $N_2$, and if $N_2$ is greater than $N_1$ by a predetermined number or more, removing the candidate nerve object.

22. The method of claim 12, wherein step (f) comprises:
   calculating a centroid point with respect to all of the pixels belonging to the bone region of the slice image;
   determining the uppermost and lowermost pixels of the bone region, and calculating a halfway point between the uppermost and lowermost pixels;
   determining whether the centroid point is located near the halfway point; and
   if the centroid point is located near the halfway point, determining the candidate nerve object above the halfway point and nearest to the centroid point, or the candidate nerve object below and nearest to the centroid point, to be a real alveolar nerve region, and if the centroid point is not near the halfway point, determining the candidate nerve object nearest to the centroid point to be an alveolar nerve region.

23. A computer readable medium having embodied thereon a computer program for identifying an alveolar nerve region in a bone image, wherein the alveolar nerve region identification comprising the steps of:
   (a) obtaining a number of 2-dimensional slice images;
   (b) detecting a binary image object corresponding to a bone region from one of the slice images;
   (c) grouping pixels of the binary image object of the bone region into clusters each containing pixels having a similar intensity;
   (d) determining clusters that have more than a predetermined minimum number of pixels, and determining a minimum labeled cluster having the lowest pixel intensity distribution among the clusters;

(e) creating a new binary image containing pixels which belong to both the bone region and the clusters having intensity distribution lower than that of the minimum labeled cluster, to extract a candidate nerve object; and (f) determining whether the candidate nerve object corresponds to the alveolar nerve region.

* * * * *